United States Patent
Kaila et al.

(10) Patent No.: US 7,465,799 B2
(45) Date of Patent: Dec. 16, 2008

(54) METHODS AND COMPOSITIONS FOR SELECTIN INHIBITION

(75) Inventors: Neelu Kaila, Lexington, MA (US); Silvano L. Debernardo, Verona, NJ (US); Kristin M. Jantz, Arlington, MA (US); Raymond T. Camphausen, Wayland, MA (US); Patricia W. Bedard, Mansfield, MA (US)

(73) Assignee: Wyeth, Madison, NJ (US)

( * ) Notice: Subject to any disclaimer, the term of this patent is extended or adjusted under 35 U.S.C. 154(b) by 516 days.

(21) Appl. No.: 10/984,093

(22) Filed: Nov. 9, 2004

(65) Prior Publication Data
US 2005/0101568 A1 May 12, 2005

Related U.S. Application Data

(60) Provisional application No. 60/518,950, filed on Nov. 10, 2003.

(51) Int. Cl.
C07D 215/38 (2006.01)
(52) U.S. Cl. ..................... 546/156; 546/153
(58) Field of Classification Search ................ 546/153, 546/156
See application file for complete search history.

(56) References Cited

U.S. PATENT DOCUMENTS

| 5,840,679 A | 11/1998 | Larsen et al. | |
| 6,083,944 A * | 7/2000 | Chatterjee et al. | 514/235.2 |
| 6,232,320 B1 | 5/2001 | Stewart et al. | |

FOREIGN PATENT DOCUMENTS

| EP | 1 422 782 A | 5/2004 |
| WO | WO 99/29705 A | 6/1999 |
| WO | WO 03/001968 A | 1/2003 |

OTHER PUBLICATIONS

Liu, Bioorg & Med Chem Lett, vol. 11, pp. 1639-1641, 2001.*
Cragoe et al., "The synthesis of 3-hydroxy-2-phenylquinoline-4, 8-dicar-boxylic acid and certain of its derivatives," *J. Org. Chem.* (1953) 18:561.
Frenette et al., "Insights into selectin function from knockout mice" *Thromb. Haemost* (1997) 78(1):60-64.
Huo "Highly efficient, general procedure for the preparation of alkylzinc reagents from unactivated alkyl bromides and chlorides" *Organic Letters* (2003) 5(4):423-425.
Johnson et al., "Absence of P-selectin delays fatty streak formation in mice" *J. Clin. Invest.* (1997) 99:1037-1043.
Kumar et al., "Recombinant soluble form of PSGL-1 accelerates thrombolysis and prevents reocclusion in a porcine model" *Circulation* (1999) 99(10):1363-1369.
Lisowski et al., "Efficient synthesis of novel 3-(Het)arylanthranilic acids via a suzuki cross-coupling reaction of 7-iodoisatin with (Het)arylboronic acids in water" *J. Org. Chem.* (2000) 65:4193-4194.

Molenaar et al., "P-selectin as a candidate target in atherosclerosis" *Biochem. Pharmacol.* (2003) 66:859-866.
Pouyani et al., "PSGL-1 recognition of P-selectin is controlled by a tyrosine sulfation consensus at the PSGL-1 amino terminus" *Cell* (1995) 83(2):333-343.
Rewcastle et al., "Potential antitumor agents. 61. Structure-activity relationships for in vivo colon 38 activity among disubstituted 9-oxo-9H-xanthene-4-acetic acids." *J. Med. Chem.* (1991) 34:217-222.
Sako et al., "A sulfated peptide segment at the amino terminus of PSGL-1 is critical for P-selectin binding" *Cell* (1995) 83(2):323-331.
Scalia et al., "Effect of recombinant soluble P-selectin glycoprotein ligand-1 on leukocyte-endothelium interation in vivo. Role in rat traumatic shock" *Circ. Res.* (1999) 84(1):93-102.
Somers et al., "Insights into the molecular basis of leukocyte tethering and rolling revealed by structures of P- and E-selectin bound to SLe(X) and PSGL-1," *Cell* (2000) 103:467-479.
Takada et al., "The cytokine-adhesion molecule cascade in ischemia/reperfusion injury of the rat kidney. Inhibition by a soluble P-selectin ligand," *J. Clin. Invest.* (1997) 99(11):2682-2690.
Wilkins et al., "Tyrosine sulfation of P-selectin glycoprotein ligand-1 is required for high affinity binding to P-selectin," *J. Biol. Chem.* (1995) 270(39):22677-22680.
Yang et al., "Induction of a Ferroelectric Sc* Liquid Crystal Phase by an Atropisomeric Dopant Derived from 4,4'-Dihydroxy-2,2'-dimethyl-6,6'-dinitrobiphenyl" *J. Am. Chem. Soc.* (1996) 118(40):9557-9561.
Berge et al., "Pharmaceutical Salts," *Journal of Pharmaceutical Sciences* (1977) 66(1): 1-19.
Greene et al., *Productive Groups In Organic Synthesis* (1991) 2d ed, John Wiley & Sons, New York.
Marvel and Hiers *Org. Synth. Coll. vol. II* (1944) 2d ed. (Blatt, A.H., ed.), John Wiley & Sons, New York, pp. 165-167.
Marvel and Hiers *Org. Synth. Coll. vol. I*, (1941) 2d ed. (Blatt, A.H., ed.), John Wiley & Sons, New York, p. 327.
*Remington's Pharmaceutical Sciences* (1980) Mack Pub. Co., Easton, PA.
Boschelli et al., "Inhibition of E-selectin-, ICAM-1-, and VCAM-1-mediated cell adhesion by benzo[b]thiophene-, benzofuran-, indole-, and naphthalene-2-carboxamides: Identification of PD 144795 as an anti-inflammatory agent," *Journal of Medicinal Chemistry* (1995) 38(22):4597-4614.
International Search Report dated May 11, 2005 for International Application No. PCT/US2004/037334.

* cited by examiner

Primary Examiner—D. Margaret Seaman

(57) ABSTRACT

The present invention relates to the field of anti-inflammatory substances, and more particularly to novel compounds that act as antagonists of the mammalian adhesion proteins known as selectins. In some embodiments, methods for treating selectin mediated disorders are provided which include administration of compound of Formula I:

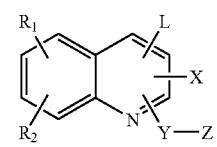

wherein the constituent variables are defined herein.

16 Claims, No Drawings

METHODS AND COMPOSITIONS FOR SELECTIN INHIBITION

CROSS-REFERENCE TO RELATED APPLICATIONS

This application claims priority to U.S. provisional application Ser. No. 60/518,950 filed Nov. 10, 2003, which is incorporated herein by reference in its entirety.

FIELD OF INVENTION

The present invention relates to the field of anti-inflammatory substances, and more particularly to novel compounds that act as antagonists of the mammalian adhesion proteins known as selectins.

BACKGROUND OF THE INVENTION

During the initial phase of vascular inflammation, leukocytes and platelets in flowing blood decrease velocity by adhering to the vascular endothelium and by exhibiting rolling behavior. This molecular tethering event is mediated by specific binding of a family of calcium dependent or "C-type" lectins, known as selectins, to ligands on the surface of leukocytes. There are also several disease states that can cause the deleterious triggering of selectin-mediated cellular adhesion, such as autoimmunity disorders, thrombotic disorders, parasitic diseases, and metastatic spread of tumor cells.

The extracellular domain of a selectin protein is characterized by an N-terminal lectin-like domain, an epidermal growth factor-like domain, and varying numbers of short consensus repeats. Three human selectin proteins have been identified, including P-selectin (formerly known as PADGEM or GMP-140), E-selectin (formerly known as ELAM-1), and L-selectin (formerly known as LAM-1). E-selectin expression is induced on endothelial cells by proinflammatory cytokines via its transcriptional activation. L-selectin is constitutively expressed on leukocytes and appears to play a key role in lymphocyte homing. P-selectin is stored in the alpha granules of platelets and the Weibel-Palade bodies of endothelial cells and therefore can be rapidly expressed on the surface of these cell types in response to proinflammatory stimuli. Selectins mediate adhesion through specific interactions with ligand molecules on the surface of leukocytes. Generally the ligands of selectins are comprised, at least in part, of a carbohydrate moiety. For example, E-selectin binds to carbohydrates having the terminal structure:

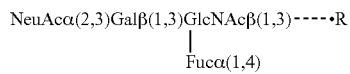

and also to carbohydrates having the terminal structures:

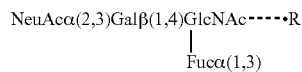

where R is the remainder of the carbohydrate chain. These carbohydrates are known blood group antigens and are commonly referred to as Sialyl Lewis x and Sialyl Lewis a, respectively. The presence of the Sialyl Lewis x antigen alone on the surface of an endothelial cell may be sufficient to promote binding to an E-selectin expressing cell. E-selectin also binds to carbohydrates having the terminal structures:

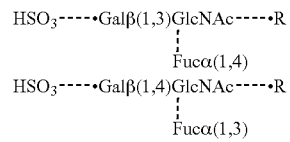

As with E-selectin, each selectin appears to bind to a range of carbohydrates with varying affinities. The strength of the selectin mediated adhesive event (binding affinity) may also depend on the density and context of the selectin on the cell surface.

Structurally diverse glycoprotein ligands, including GlyCAM-1, CD34, ESL-1 and PSGL-1 can bind to selectins with apparent high affinity. PSGL-1 is a mucin-like homodimeric glycoprotein expressed by virtually all subsets of leukocytes and is recognized by each of the three selectins. However PSGL-1 appears to be unique in that it is the predominant high affinity P-selectin ligand on leukocytes. High affinity P-selectin binding to PSGL-1 requires both a SLex containing O-glycan and one or more tyrosine sulfate residues within the anionic N-terminus of the PSGL-1 polypeptide (See Sako, D., et al. *Cell* 1995; 82(2): 323-331; Pouyani, N., et al., *Cell* 1995; 82(2): 333-343; Wilkins, P. P., et al., *J. Biol. Chem.* 1995; 270:39 22677-22680, each of which is incorporated herein by reference in its entirety). L-Selectin also recognizes the N-terminal region of PSGL-1 and has similar sulfation-dependent binding requirements to that of P-selectin. The ligand requirements of E-selectin appear to be less stringent as it can bind to the SLex containing glycans of PSGL-1 and other glycoproteins. Despite the fact that P-selectin knockout and P/E selectin double knockout mice show elevated levels neutrophils in the blood, these mice show an impaired DTH response and delayed thioglycolate induced peritonitis (TIP) response (See Frenette, P. S., et al., *Thromb Haemost* 1997; 78:1, 60-64, incorporated herein by reference in its entirety). Soluble forms of PSGL-1 such as rPSGL-Ig have shown efficacy in numerous animal models (See Kumar, A., et. al., *Circulation.* 1999, 99(10) 1363-1369; Takada, M., et. al. *J. Clin. Invest* 1997, 99(11), 2682-2690; Scalia, R., et al., *Circ Res.* 1999, 84(1), 93-102, each of which is incorporated herein by reference in its entirety.

In addition, P-selectin ligand proteins, and the gene encoding the same, have been identified. See U.S. Pat. No. 5,840, 679, incorporated herein by reference in its entirety. As demonstrated by P-selectin/LDLR deficient mice, inhibition of P-selectin represents a useful target for the treatment of atherosclerosis (See Johnson, R. C., et al., *J. Clin. Invest.* 1997 99 1037-1043, incorporated herein by reference in its entirety). An increase in P-selectin expression has been reported at the site of atherosclerotic lesions, and the magnitude of the P-selectin expression appears to correlate with the lesion size. It is likely that the adhesion of monocytes, mediated by P-selectin, contributes to atherosclerotic plaque progression (See Molenaar, T. J. M., et al., *Biochem. Pharmacol.* 2003 (66) 859-866, incorporated herein by reference in its entirety). Given the role of selectins in numerous important biological processes, including inflammation and adhesion processes, and in disorders such as atherlosclerosis, it can be seen that there is a continuing need for new selectin inhibitors that can be useful in the treatment of a variety of diseases and disorders that are characterized by, or that involve selectin activity. This invention is directed to these, as well as other, important ends.

SUMMARY OF THE INVENTION

In one aspect, the present invention provides compounds and methods for treating mammals having conditions characterized by selectin mediated intercellular adhesion processes. In one aspect, the invention provides compounds useful in the methods, that have the Formula I:

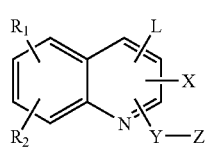

wherein:
L is $CO_2H$, an ester thereof, or a pharmaceutically acceptable acid mimetic;
Y is O, $(CR_3R_4)_p$ or $NR_5$;
p is 1 to 3;
X is hydrogen, OH, $OR_3$, $OC_{1-6}$alkyl, $OC(=O)$-aryl, $OC(=O)C_{1-6}$alkyl, $OC(=O)OC_{1-6}$ alkyl, or $NR_3R_3$;
each $R_1$, $R_2$, $R_3$, $R_3$ and $R_4$ is independently hydrogen, $C_{1-6}$ alkyl, $C_{1-6}$ perhaloalkyl,
$OC_{1-6}$ alkyl, $OC_{1-6}$ perhaloalkyl, halogen, thioalkyl, CN, OH, SH, $(CH_2)_nOSO_3H$, $(CH_2)_nSO_3H$, $(CH_2)_nCO_2R_6$, $OSO_3R_6$, $SO_2R_6$, $SO_3R_6$, $PO_3R_6R_7$, $(CH_2)_nSO_2NR_8R_9$, $(CH_2)_nC(=O)NR_8R_9$, $NR_8R_9$, $C(=O)R_{12}$, aryl, heterocyclo, $C(=O)$aryl, $C(=O)$heterocyclo, $OC(=O)$aryl, $OC(=O)$heterocyclo, Oaryl, Oheterocyclo, arylalkyl, $C(=O)$arylalkyl, $OC(=O)$arylalkyl, Oarylalkyl, alkenyl, alkynyl, or $NHCOR_8$, wherein any of said alkyl, Oalkyl, aryl, heterocyclo, $C(=O)$aryl, $C(=O)$heterocyclo, O—C$(=O)$aryl, O—C$(=O)$heterocyclo, O-aryl, O-heterocyclo, arylalkyl, $C(=O)$arylalkyl, O—C$(=O)$arylalkyl, O-arylalkyl, alkenyl or alkynyl can optionally be substituted with up to three substituents selected from halogen, $C_{1-6}$alkyl, $OC_{1-6}$alkyl and CN;
each $R_6$ and $R_7$ is independently hydrogen or $C_{1-6}$ alkyl that is optionally substituted with up to three substituents selected from OH, $CF_3$, SH and halogen;
each $R_5$, $R_8$ and $R_9$ is independently hydrogen, $C_{1-6}$ alkyl, $C_{1-6}$ haloalkyl, thioalkyl, OH, $(CH_2)_lOSO_3H$, $(CH_2)_lSO_3R_{10}$, $(CH_2)_nCO_2R_{10}$, $SO_3R_{10}$, $PO_3R_{10}R_{11}$, $(CH_2)_nSO_2(CH_2)_n$ $NR_{10}R_{11}$, $(CH_2)_nCONR_{10}R_{11}$, $COR_{10}$, aryl, heterocyclo, $C(=O)$aryl, $C(=O)$heterocyclo, O—C$(=O)$aryl, O—C$(=O)$heterocyclo, Oaryl, Oheterocyclo, arylalkyl, $C(=O)$arylalkyl, $OC(=O)$arylalkyl, Oarylalkyl, alkenyl, or alkynyl, wherein any of said alkyl, aryl, heterocyclo, $C(=O)$aryl, $C(=O)$heterocyclo, $OC(=O)$aryl, $OC(=O)$heterocyclo, Oaryl, Oheterocyclo, arylalkyl, $C(=O)$arylalkyl, $OC(=O)$arylalkyl, Oarylalkyl, alkenyl or alkynyl can optionally be substituted with up to three substituents selected from halogen, $C_{1-6}$ alkyl, $OC_{1-6}$ alkyl and CN;
each n is an independently selected integer from 0 to 6;
each l is an independently selected integer from 1 to 6;
each $R_{10}$ and $R_{11}$ is independently hydrogen and $C_{1-6}$alkyl that is optionally substituted with up to three substituents selected from OH, $CF_3$, SH and halogen;
each $R_{12}$ is independently hydrogen, $C_{1-6}$ alkyl, $C_{1-6}$ perhaloalkyl, $OC_{1-6}$ alkyl, $OC_{1-6}$ perhaloalkyl, thioalkyl, OH, $(CH_2)_lOSO_3H$, $(CH_2)_lSO_3H$, $(CH_2)_lCO_2R_6$, $(CH_2)_lSO_2NR_8R_9$, $(CH_2)_lC(=O)NR_8R_9$, $NR_8R_9$, alkenyl, alkynyl, or $NHCOR_8$, wherein any of said alkyl, Oalkyl, alkenyl or alkynyl can optionally be substituted with up to three substituents selected from halogen, $C_{1-6}$ alkyl, $OC_{1-6}$ alkyl and CN; and
Z is aryl, arylalkyl, heteroaryl or heterocyclo, wherein each of said aryl, arylalkyl, heteroaryl and heterocyclo is optionally substituted.

In some preferred embodiments, the compounds have the Formula II:

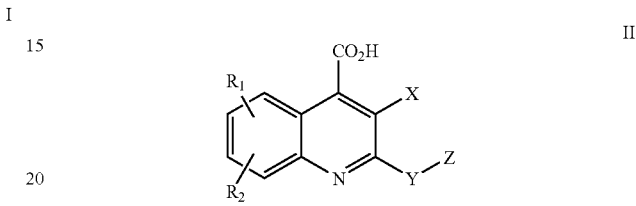

In some embodiments, Y is $CR_3R_4$, preferably $CH_2$. In some embodiments, Y is $CH_2$ and X is OH. In further embodiments, Z is selected from:

(a) a five-membered heterocyclic ring containing one to three ring heteroatoms selected from N, S or O; wherein said five-membered heterocyclic ring is optionally substituted by from 1 to 3 substituents selected from halogen, $C_{1-10}$ alkyl, $OC_{1-10}$ alkyl, $NO_2$, $NH_2$, CN, $CF_3$, and $CO_2H$;

(b) a six-membered heterocyclic ring containing one to three ring heteroatoms selected from N, S or O; wherein said six-membered heterocyclic ring is optionally substituted by from 1 to 3 substituents selected from halogen, $C_{1-10}$ alkyl, $OC_{1-10}$ alkyl, CHO, $CO_2H$, $C(=O)R_{20}$, $SO_2R_{20}$, $NO_2$, $NH_2$, CN, $CF_3$ and OH;

(c) a bicyclic ring moiety optionally containing from 1 to 3 ring heteroatoms selected from N or O; wherein said bicyclic ring moiety is optionally substituted by from 1 to 3 substituents selected from halogen, $C_{1-6}$ alkyl, $OC_{1-6}$ alkyl, CHO, $NO_2$, $NH_2$, CN, $CF_3$, $CO_2H$, $C(=O)R_{20}$, $SO_2R_{20}$, and OH; and (d) a benzyl, naphthyl, or phenyl ring, each of which is optionally substituted by from 1 to 3 substituents selected from halogen, $C_{1-6}$ alkyl, phenyl, benzyl, Ophenyl, Obenzyl, $SO_2NH_2$, $SO_2NH(C_{1-6}$ alkyl), $SO_2N(C_{1-6}$ alkyl)$_2$, $CH_2COOH$, $CO_2H$, $CO_2Me$, $CO_2Et$, $CO_2iPr$, $C(=O)NH_2$, $C(=O)NH(C_{1-6}$ alkyl), $C(=O)N(C_{1-6}$ alkyl)$_2$, OH, $SC_{1-6}$ alkyl, $OC_{1-6}$ alkyl, $NO_2$, $NH_2$, $CF_3$, and CN;

wherein each $R_{20}$ is independently selected from the group consisting of $C_{1-10}$ alkyl, $OC_{1-10}$ alkyl and $NR_6R_7$.

In some embodiments, Z is aryl.

In some embodiments, $R_1$ and $R_2$ are each independently hydrogen, $C_{1-6}$ alkyl, $C_{1-6}$ perhaloalkyl, $OC_{1-6}$ alkyl, $OC_{1-6}$ perhaloalkyl, halogen, thioalkyl, CN, OH, SH, $(CH_2)_n$ $OSO_3H$, $(CH_2)_nSO_3H$, $(CH_2)_nCO_2R_6$, $OSO_3R_6$, $SO_3R_6$, $PO_3R_6R_7$, $(CH_2)_nSO_2NR_8R_9$, $(CH_2)_nC(=O)NR_8R_9$, $NR_8R_9$, aryl, heterocyclo, $C(=O)R_{12}$, $C(=O)$aryl, $C(=O)$heterocyclo, $OC(=O)$aryl, $OC(=O)$heterocyclo, Oaryl, Oheterocyclo, $C(=O)$arylalkyl, $OC(=O)$arylalkyl, Oarylalkyl, alkenyl, alkynyl, or $NHCOR_8$.

In some preferred embodiments, Y is $CH_2$, X is OH, and Z is selected from (a), (b), (c) and (d) above:

In some preferred embodiments, the compounds have the Formula III:

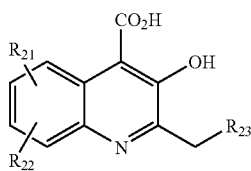

wherein:

$R_{21}$ and $R_{22}$ are independently, hydrogen, halogen, OH, CN, SH, $C_{1-6}$ alkyl, $OC_{1-6}$ alkyl, $C_{1-6}$ perhaloalkyl, $C_{1-6}$ thioalkyl, aryl or heteroaryl;

wherein said aryl and said heteroaryl can each optionally be substituted with up to three substituents selected from halogen, OH, CN, SH, $NH_2$, $C_{1-6}$ alkyl, $OC_{1-6}$ alkyl, $C_{1-6}$ perhaloalkyl and $C_{1-6}$ thioalkyl; and wherein said $C_{1-6}$ alkyl, $OC_{1-6}$ alkyl and $C_{1-6}$ thioalkyl can each optionally be substituted with up to three substituents selected from halogen, OH, CN, SH, $NH_2$, $OC_{1-6}$ alkyl, $C_{1-6}$ perhaloalkyl and $C_{1-6}$ thioalkyl; and $R_{23}$ is aryl or heteroaryl, wherein said aryl and said heteroaryl can each optionally be substituted with up to three substituents selected from halogen, OH, CN, SH, $NH_2$, $C_{1-6}$ alkyl, $OC_{1-6}$ alkyl, $C_{1-6}$ perhaloalkyl and $C_{1-6}$ thioalkyl.

In some embodiments, $R_{21}$ and $R_{22}$ are each independently hydrogen, $C_{1-6}$ alkyl, halogen, aryl, heteroaryl, or $OC_{1-6}$ alkyl, wherein said heteroaryl is 3-furanyl or 3-thiophenyl and said aryl is unsubstituted phenyl; and wherein said $C_{1-6}$ alkyl and said $OC_{1-6}$ alkyl can each optionally be substituted with up to three substituents selected from halogen, OH, CN, SH, $NH_2$, $OC_{1-6}$ alkyl, $C_{1-6}$ perhaloalkyl and $C_{1-6}$ thioalkyl; and $R_{23}$ is a phenyl group substituted at the 4'-position with halogen, $C_{1-6}$ alkyl, $SC_{1-6}$ alkyl, or $OC_{1-6}$ alkyl.

In further embodiments, $R_1$ and $R_2$ are located on the 7 and 8 positions of the quinoline ring and are independently selected from the group consisting of H, methyl, and unsubstituted phenyl; and $R_{23}$ is phenyl substituted at the 4'-position with Cl or $OCF_3$.

In further embodiments, $R_1$ is located at the 7 position of the quinoline ring and $R_2$ is located at the 8 position of the quinoline ring; and either $R_1$ is $CH_3$, $R_2$ is $CH_3$ and $R_{23}$ is 4-chlorophenyl; or $R_1$ is H, $R_2$ is unsubstituted phenyl and $R_{23}$ is 4-chlorophenyl.

In some embodiments, the invention provides the compounds a) 2-(4-Chloro-benzyl)-3-hydroxy-8-trifluoromethyl-quinoline-4-carboxylic acid; b) 2-(4-Chloro-benzyl)-3-hydroxy-8-trifluoromethoxy-quinoline-4-carboxylic acid; c) 2-(4-Chlorobenzyl)-3-hydroxy-8-isopropylquinoline-4-carboxylic acid; d) 2-(4-Chlorobenzyl)-3-hydroxy-8-methylquinoline-4-carboxylic acid; e) 2-(4-Chlorobenzyl)-8-ethyl-3-hydroxyquinoline-4-carboxylic acid; f) 2-(4-Chlorobenzyl)-3-hydroxy-8-(thien-3-yl)quinoline-4-carboxylic acid; g) 8-Bromo-2-(4-chlorobenzyl)-3-hydroxyquinoline-4-carboxylic acid; h) 8-(sec-Butyl)-2-(4-chlorobenzyl)-3-hydroxyquinoline-4-carboxylic acid; i) 2-(4-Chlorobenzyl)₃-hydroxy-6-phenylquinoline-4-carboxylic acid; j) 2-(4-Chlorobenzyl)-8-(fur-3-yl)-3-hydroxyquinoline-4-carboxylic acid; k) 2-(4-Chlorobenzyl)-8-fluoro-3-hydroxyquinoline-4-carboxylic acid; l) 2-(4-Chlorobenzyl)-8-fluoro-3-hydroxyquinoline-4-carboxylic acid; m) 2-(4-Chloro-benzyl)-3-hydroxy-8-(2,2,2-trifluoro-1-hydroxy-1-trifluoromethyl-ethyl)-quinoline-4-carboxylic acid; and n) 2-(4-Chloro-benzyl)-3-hydroxy-quinoline-4-carboxylic acid.

Also provided in accordance with the present invention are compositions comprising a pharmaceutically effective amount of a compound according of the invention, and a pharmaceutically acceptable carrier or excipient.

The present invention also provides methods for using the compounds disclosed herein. In some embodiments, the invention provides methods of inhibiting selectin-mediated intracellular adhesion in a mammal comprising administering to the mammal an effective amount of a compound of the invention.

In further embodiments, the invention provides methods of inhibiting selectin-mediated intracellular adhesion associated with a disease, disorder, condition or undesired process in a mammal, the method comprising administering to the mammal an effective amount of a compound of the invention.

In some preferred embodiments, the disease, disorder, condition or undesired process is inflammation, infection, metastasis, an undesired immunological process, or an undesired thrombotic process.

In some embodiments, the disease, disorder, condition or undesired process is atherosclerosis, restenosis, myocardial infarction, Reynauld's syndrome, inflammatory bowel disease, osteoarthritis, acute respiratory distress syndrome, asthma, emphysema, delayed type hypersensitivity reaction, thermal injury, experimental allergic encephalomyelitis, multiple organ injury syndrome secondary to trauma, neutrophilic dermatosis (Sweet's disease), glomerulonephritis, ulcerative colitis, Crohn's disease, necrotizing enterocolitis, cytokine-induced toxicity, gingivitis, periodontitis, hemolytic uremic syndrome, psoriasis, systemic lupus erythematosus, autoimmune thyroiditis, multiple sclerosis, rheumatoid arthritis, Grave's disease, immunological-mediated side effects of treatment associated with hemodialysis or leukapheresis, granulocyte transfusion associated syndrome, deep vein thrombosis, unstable angina, transient ischemic attacks, peripheral vascular disease, metastasis associated with cancer or congestive heart failure.

In some embodiments, the disease, disorder, condition or undesired process is an undesired infection process mediated by a bacteria, a virus, or a parasite, for example gingivitis, periodontitis, hemolytic uremic syndrome, or granulocyte transfusion associated syndrome.

In further embodiments, the disease, disorder, condition or undesired process is metastasis associated with cancer.

In further embodiments, the disease, disorder, condition or undesired process is a disease or disorder associated with an undesired immunological process, for example psoriasis, systemic lupus erythematosus, autoimmune thyroiditis, multiple sclerosis, rheumatoid arthritis, Grave's disease and immunological-mediated side effects of treatment associated with hemodialysis or leukapheresis.

In further embodiments, the disease, disorder, condition or undesired process is a condition associated with an undesired thrombotic process, for example deep vein thrombosis, unstable angina, transient ischemic attacks, peripheral vascular disease, or congestive heart failure.

In some further embodiments, the invention provides methods of ameliorating an undesired immunological process in a transplanted organ comprising administering to said organ an immunosupressive agent in conjunction with a compound of the invention.

In some further embodiments, the invention provides methods comprising identifying a human, mammal or animal as having a biomarker for a disease or disorder involving selectin-mediated intracellular adhesion; and administering to said human, mammal or animal a therapeutically effective amount of a compound as disclosed herein. In some embodiments, the biomarker is one or more of CD 40, CD 40 Ligand, MAC-1, TGF beta, ICAM, VCAM, IL-1, IL-6, IL-8, Eotaxin, RANTES, MCP-1, PlGF, CRP, SAA, and platelet monocyte aggregtates.

DETAILED DESCRIPTION

The present invention provides, in some embodiments, methods and compounds for antagonizing selecting-mediated intercellular adhesion. Interfering or preventing such intercellular adhesion is useful both in the treatment of a variety of diseases and disorders, as well as for ameliorating one or more symptoms of such diseases or disorders. Thus, in some embodiments, the present invention provides methods of inhibiting selectin-mediated intracellular adhesion in a mammal, particularly where such selectin-mediated intracellular adhesion is associated with a disease, disorder, condition or undesired process in a mammal, comprising administering to the mammal an effective amount of a compound of the invention.

Diseases, disorders, conditions and undesired processes amendable to the methods of the invention include all those that are wholly or in part characterized by undesired selectin-mediated intercellular adhesion, for example inflammation, infection (for example mediated by a bacteria, a virus, or a parasite, including for example gingivitis, periodontitis, hemolytic uremic syndrome, and granulocyte transfusion associated syndrome), metastasis (for example associated with cancer), undesired immunological processes, and undesired thrombotic processes. Nonlimiting examples of the foregoing include atherosclerosis, restenosis, myocardial infarction, Reynauld's syndrome, inflammatory bowel disease, osteoarthritis, acute respiratory distress syndrome, asthma, emphysema, delayed type hypersensitivity reaction, thermal injury such as burns or frostbite, experimental allergic encephalomyelitis, multiple organ injury syndrome secondary to trauma, neutrophilic dermatosis (Sweet's disease), glomerulonephritis, ulcerative colitis, Crohn's disease, necrotizing enterocolitis, cytokine-induced toxicity, gingivitis, periodontitis, hemolytic uremic syndrome, psoriasis, systemic lupus erythematosus, autoimmune thyroiditis, multiple sclerosis, rheumatoid arthritis, Grave's disease, immunological-mediated side effects of treatment associated with hemodialysis or leukapheresis, granulocyte transfusion associated syndrome, deep vein thrombosis, unstable angina, transient ischemic attacks, peripheral vascular disease, stroke and congestive heart failure.

The infection process involves selectin-mediated intercellular adhesion. Thus, the present invention also provides methods of treating or preventing an undesired infection process in a mammal, comprising administering to said mammal a compound of the invention. The infection can be mediated by a bacteria, a virus, or a parasite, and examples of such infection processes include gingivitis, periodontitis, hemolytic uremic syndrome, and granulocyte transfusion associated syndrome.

Further examples of diseases and disorders that involve selectin-mediated intercellular adhesion include metastasis in cancer, and diseases or disorders associated with an undesired immunological processes, for example psoriasis, systemic lupus erythematosus, autoimmune thyroiditis, multiple sclerosis, rheumatoid arthritis, Grave's disease and immunological-mediated side effects of treatment associated with hemodialysis or leukapheresis.

A further example is in organ transplantation, wherein patients generally receive immunosupressive therapy to minimize the possibility of rejection of the organ. Typical immunosupressive agents used for such therapeutic regimes include cyclosporine, rapamycin and tacrolimus. In some embodiments of the invention, a compound of the invention can be administered to the patient to receive the organ transplant in conjunction with one or more such immunosupressive agents. Thus, in some embodiments, the compound of the invention can be administered to an organ for transplant, by, for example, administering the compound to the patient prior to transplant, to the patient after transplant, or directly to the transplanted organ itself either before or after transplant (for example by perfusion), or in any combination. Thus, in preferred embodiments, the compound of the invention can be administered to an organ in conjunction with one or more immunosupressive agents; i.e., the compound can be administered at the same time as an immunosupressive agent, or at any time during which an immunosupressive agent is present in effective amounts in the organ or patient.

Further examples of processes involving selectin-mediated intercellular adhesion which are amenable to the methods of the invention include conditions associated with an undesired thrombotic process, for example deep vein thrombosis, unstable angina, transient ischemic attacks, peripheral vascular disease, or congestive heart failure.

The compounds of the invention also find use in the treatment of sickle syndromes, for example sickle cell anemia, and in ameliorating one or more symptoms of such disorders.

In some embodiments, the compounds of the invention find use in treatment of the aforementioned diseases and/or disorders when administered in combination with other therapeutic agents. For example, in some embodiments, the compounds of the invention can beneficially be administered to patients with vascular diseases, for example CAD (coronary artery disease, including but not limited to acute coronary syndrome (e.g., MI and stroke)), peripheral vascular disease including PAD (peripheral artery disease), and deep vein thrombosis, along with an anti-platelet agent, such as Plavix or aspirin, and/or lipid modulators such as, for example statins. Other suitable anti-platelet agents and lipid modulators will be apparent to those of skill in the art.

The compounds of the invention further find use in the treatment of diseases and disorders implicated by biomarkers as are known in the art. Nonlimiting biomarkers include, for example, CD 40, CD 40 Ligand, MAC-1, TGF beta, ICAM, VCAM, IL-1, IL-6, IL-8, Eotaxin, RANTES, MCP-1, PlGF, CRP and SAA, as well as platelet monocyte aggregtates.

In accordance with some preferred embodiments, methods of the invention include administration of one or more compounds having the Formula I:

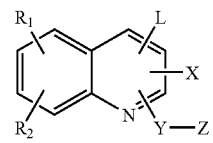

wherein the constituent variables are as defined above.

In some embodiments, Y-Z is located at the 2-position of the quinoline. In further embodiments, X is located at the 3-position of the quinoline. In further embodiments, L is located at the 4-position of the quinoline. In some embodiments, L, Y-Z and X are located at the 4, 3 and 2-positions of the quinoline, respectively.

In some embodiments of the compounds and methods of the invention, the compound of Formula I has the Formula II:

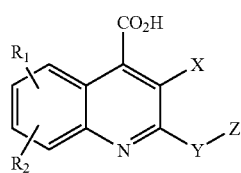

II wherein the constituent variables are as defined above.

In some further embodiments, the compound of Formula I has the Formula III:

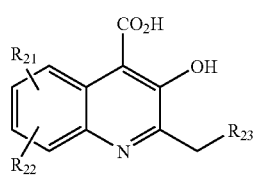

III wherein the constituent variables are as defined above.

In some embodiments of the compounds and methods of the invention, Y is $CR_3R_4$, preferably $CH_2$, and more preferably where X is OH. In some particularly preferred embodiments, Y is $CH_2$, X is OH and Z is aryl, more preferably phenyl or substituted phenyl. In some especially preferred embodiments, Z is phenyl substituted at the 4'-position. In some embodiments, such 4'-substitutents are small hydrophobic groups such as halogens, $C_{1-6}$ alkyl, $C_{1-6}$ perhaloalkyl, $OC_{1-6}$ alkyl, $OC_{1-6}$ perhaloalkyl, $C_{1-6}$ thioalkyl, CN, alklysulfonamides, and mono- and di-alkylamines.

In some embodiments of the compounds and methods of the invention where Y is $CH_2$ and X is OH, Z is selected from:

(a) a five-membered heterocyclic ring containing one to three ring heteroatoms selected from N, S or O; wherein said five-membered heterocyclic ring is optionally substituted by from 1 to 3 substituents selected from halogen, $C_1$-$C_{10}$ alkyl, $OC_1$-$C_{10}$ alkyl, $NO_2$, $NH_2$, CN, $CF_3$, and $CO_2H$;

(b) a six-membered heterocyclic ring containing one to three ring heteroatoms selected from N, S or O; wherein said six-membered heterocyclic ring is optionally substituted by from 1 to 3 substituents selected from halogen, $C_1$-$C_{10}$ alkyl, $OC_1$-$C_{10}$ alkyl, CHO, $CO_2H$, C(=O)$R_{20}$, $SO_2R_{20}$, $NO_2$, $NH_2$, CN, $CF_3$ and OH;

(c) a bicyclic ring moiety optionally containing from 1 to 3 ring heteroatoms selected from N or O; wherein said bicyclic ring moiety is optionally substituted by from 1 to 3 substituents selected from halogen, $C_1$-$C_6$ alkyl, $OC_1$-$C_6$ alkyl, CHO, $NO_2$, $NH_2$, CN, $CF_3$ $CO_2H$, C(=O)$R_{20}$, $SO_2R_{20}$, and OH; and (d) a benzyl, naphthyl, or phenyl ring, each of which is optionally substituted by from 1 to 3 substituents selected from halogen, $C_1$-$C_6$ alkyl, phenyl, benzyl, Ophenyl, Obenzyl, $SO_2NH_2$, $SO_2NH(C_{1-6}$ alkyl), $SO_2N(C_{1-6}$ alkyl$)_2$, $CH_2COOH$, $CO_2H$, $CO_2Me$, $CO_2Et$, $CO_2iPr$, C(=O)$NH_2$, C(=O)NH($C_{1-6}$alkyl), C(=O)N($C_{1-6}$ alkyl$)_2$, OH, S—$C_{1-6}$ alkyl, $OC_{1-6}$ alkyl, $NO_2$, $NH_2$, $CF_3$, and CN.

In some preferred embodiments, preferably but not limited to those wherein Y is $CH_2$, X is OH, and Z is phenyl or substituted phenyl as described above, $R_1$ and $R_2$ are small hydrophobic groups such as halogens, $C_{1-6}$ alkyl, $C_{1-6}$ perhaloalkyl, $OC_{1-6}$ alkyl, $OC_{1-6}$ perhaloalkyl, $C_{1-6}$thioalkyl, CN, $C_{1-6}$ alklysulfonamides, $C_{1-6}$ mono- and di-alkylamines, or aryl or substituted aryl having up to 8 carbon atoms, wherein the substituents are selected from halogen, $C_{1-10}$ alkyl, $OC_{1-10}$ alkyl, CHO, $CO_2H$, $NO_2$, $NH_2$, CN, $CF_3$ and —OH. In some embodiments, one of $R_1$ and $R_2$ is a small hydrophobic group, and the other of $R_1$ and $R_2$ is aryl or substituted aryl having up to 8 carbon atoms.

In some embodiments where the compound of Formula I has the Formula III, $R_{21}$, and $R_{22}$ are independently selected from the group consisting of H, $C_{1-6}$ alkyl, halogen, aryl, heteroaryl, and $OC_{1-6}$ alkyl wherein said heteroaryl is 3-furanyl or 3-thiophenyl and said aryl is unsubstituted phenyl; and $R_{23}$ is a phenyl group substituted at the 4'-position with halogen, $C_{1-6}$ alkyl, $SC_{1-6}$ alkyl, or $OC_{1-6}$ alkyl.

In further such embodiments, $R_{21}$, and $R_{22}$ are located on the 7 and 8 positions of the quinoline ring and are independently selected from the group consisting of H, methyl, and unsubstituted phenyl; and $R_{23}$ is phenyl substituted at the 4'-position with Cl or $OCF_3$.

In still further such embodiments, $R_{21}$ is located at the 7 position of the quinoline ring and $R_{22}$ is located at the 8 position of the quinoline ring; and either $R_{21}$ is $CH_3$; $R_{22}$ is $CH_3$ and $R_{23}$ is 4-chlorophenyl; or $R_{21}$ is H; $R_{22}$ is unsubstituted phenyl and $R_{23}$ is 4-chlorophenyl.

In some embodiments wherein the compound has the Formula III, $R_{21}$ and $R_{22}$ are independently selected from the group consisting of H, $C_{1-6}$ alkyl, halogen, aryl, heteroaryl, and $OC_{1-6}$ alkyl wherein said heteroaryl is 3-furanyl or 3-thiophenyl and said aryl is unsubstituted phenyl; and said $C_{1-6}$ alkyl and said $OC_{1-6}$ alkyl can each optionally be substituted with up to three substituents selected from halogen, OH, CN, SH, $NH_2$, $OC_{1-6}$ alkyl, $C_{1-6}$ perhaloalkyl and $C_{1-6}$ thioalkyl; and $R_{23}$ is a phenyl group substituted at the 4'-position with halogen, $C_{1-6}$ alkyl, $SC_{1-6}$ alkyl, or $OC_{1-6}$ alkyl.

The present invention further provides, in some preferred embodiments, the compounds 2-(4-chloro-benzyl)-3-hydroxy-7,8,-dimethyl-quinoline-4-carboxylic acid, 2-(4-chloro-benzyl)-3-hydroxy-8-phenyl-quinoline-4-carboxylic acid, or is selected from 2-(4-chloro-benzyl)-3-hydroxy-8-trifluoromethyl-quinoline-4-carboxylic acid, 2-(4-chloro-benzyl)-3-hydroxy-8-trifluoromethoxy-quinoline-4-carboxylic acid, 2-(4-chlorobenzyl)-3-hydroxy-8-isopropylquinoline-4-carboxylic acid, 2-(4-chlorobenzyl)-3-hydroxy-8-methylquinoline-4-carboxylic acid, 2-(4-chlorobenzyl)-8-ethyl-3-hydroxyquinoline-4-carboxylic acid, 2-(4-chlorobenzyl)-3-hydroxy-8-(thien-3-yl)quinoline-4-carboxylic acid, 8-bromo-2-(4-chlorobenzyl)-3-hydroxyquinoline-4-carboxylic acid, 8-(sec-butyl)-2-(4-chlorobenzyl)-3-hydroxyquinoline-4-carboxylic acid, 2-(4-chlorobenzyl)3-hydroxy-6-phenylquinoline-4-carboxylic acid, 2-(4-chlorobenzyl)-8-(fur-3-yl)-3-hydroxyquinoline-4-carboxylic acid, 2-(4-chlorobenzyl)-8-fluro-3-hydroxyquinoline-4-carboxylic acid; and 2-(4-chlorobenzyl)-8-fluoro-3-hydroxyquinoline-4-carboxylic acid, which are useful in the methods of the invention.

It will be understood that compounds of Formulas I, II and III can have one or more chiral centers, and exist as enantiomers or diastereomers. The invention is to be understood to extend to all such enantiomers, diastereomers and mixtures thereof, including racemates.

It is contemplated that the present invention also include all possible protonated and unprotonated forms of the compounds described herein, as well as solvates, tautomers and pharmaceutically acceptable salts thereof.

In some embodiments, substituent L is $CO_2H$, an ester thereof, or a pharmaceutically acceptable acid mimetic. As used herein, the term "acid mimetic" is intended to include moieties that mimic acid functionality in biological molecules. Examples of such acid mimetics are known in the art, and include without limitation —OH and those shown below:

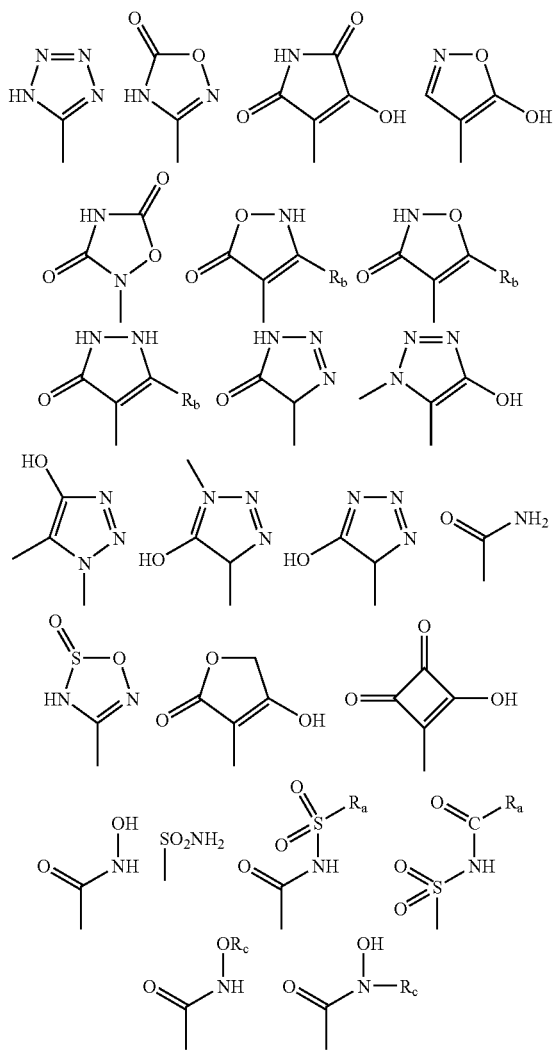

wherein:

$R_a$ is selected from $—CF_3$, $CH_3$, phenyl or benzyl, where the phenyl or benzyl is optionally substituted by up to three groups selected from $C_{1-6}$ alkyl, $C_{1-6}$ alkoxy, $C_{1-6}$ thioalkyl, $—CF_3$, halogen, —OH or COOH;

$R_b$ is selected from $—CF_3$, $—CH_3$, $—NH_2$, phenyl or benzyl, where the phenyl or benzyl is optionally substituted by up to three groups selected from $C_{1-6}$ alkyl, $C_{1-6}$ alkoxy, $C_{1-6}$ thioalkyl, $—CF_3$, halogen, —OH or COOH; and $R_c$ is selected from $—CF_3$ and $C_{1-6}$ alkyl.

Ester forms of the present compounds (for example compounds where L is an ester of $CO_2H$) include the pharmaceutically acceptable ester forms known in the art including those which can be metabolized into the free acid form, such as a free carboxylic acid form, in the animal body, such as the corresponding alkyl esters (e.g., alkyl of 1 to 10 carbon atoms), cycloalkyl esters (e.g., of 3-10 carbon atoms), aryl esters (e.g., of 6-20 carbon atoms) and heterocyclic analogues thereof (e.g., of 3-20 ring atoms, 1-3 of which can be selected from oxygen, nitrogen and sulfur heteroatoms) can be used according to the invention, where alkyl esters, cycloalkyl esters and aryl esters are preferred and the alcoholic residue can carry further substituents. $C_1$-$C_8$ alkyl esters, preferably $C_1$-$C_6$ alkyl esters, such as the methyl ester, ethyl ester, propyl ester, isopropyl ester, butyl ester, isobutyl ester, t-butyl ester, pentyl ester, isopentyl ester, neopentyl ester, hexyl ester, cyclopropyl ester, cyclopropylmethyl ester, cyclobutyl ester, cyclopentyl ester, cyclohexyl ester, or aryl esters such as the phenyl ester, benzyl ester or tolyl ester are particularly preferred.

As used herein, the term alkyl as a group or part of a group is intended to denote hydrocarbon groups, e.g., of 1-20, such as 1-6, carbon atoms, including straight chain, branched and cyclic hydrocarbons, including for example but not limited to methyl, ethyl, n-propyl, isopropyl, cyclopropyl, n-butyl, sec-butyl, tert-butyl, cyclobutyl, cyclopropylmethyl, n-pentyl, isopentyl, tert-pentyl, cyclopentyl, cyclopentylmethyl, n-hexyl, cyclohexyl, and the like. Throughout this specification, it should be understood that the term alkyl is intended to encompass both non-cyclic hydrocarbon groups and cyclic hydrocarbon groups. In some embodiments of the compounds of the invention, alkyl groups are non-cyclic. In further embodiments, alkyl groups are cyclic, and in further embodiments, alkyl groups are both cyclic and noncyclic.

Alkyl groups of the compounds and methods of the invention can include optional substitution with from one halogen up to perhalogenation. In some embodiments, perfluoro groups are preferred. Examples of alkyl groups optionally substituted with halogen include $CF_3$, $CH_2CF_3$, $CCl_3$, $CH_2CH_2CF_2CH_3$, $CH(CF_3)_2$, and $(CH_2)_6—CF_2CCl_3$.

As used herein, the term alkenyl is intended to denote alkyl groups that contain at least one double bond, e.g., 2-20, preferably 2-6 carbon atoms, including for example but not limited to vinyl, allyl, 2-methyl-allyl, 4-but-3-enyl, 4-hex-5-enyl, 3-methyl-but-2-enyl, cyclohex-2-enyl and the like.

As used herein, the term alkynyl is intended to denote alkyl groups that include at least one triple bond, e.g., 2-20, preferably 2-6 carbon atoms including for example but not limited to but-1-yne, propyne, pent-2-yne, ethynyl-cyclohexyl and the like.

Alkyl, alkenyl and alkynyl groups as defined above may also be optionally substituted i.e., they can optionally bear further substituent groups. Some preferred substituent groups include hydroxy, alkoxy (i.e., O-alkyl, preferably O—$C_{1-6}$ alkyl), mono-, di- or trihaloalkoxy (e.g., —O—$CX_3$ where X is halogen), $—(CH_2)_nNH_2$, and $—(CH_2)_nNHBoc$.

At various places in the present specification substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, propyl, isopropyl, n-butyl, sec-butyl, isobutyl, etc. As used herein, the term halogen has its normal meaning of group seven elements, including F, Cl, Br and I.

As used herein, the term "carbocyclic ring" is intended to denote a saturated, partially saturated or aromatic ring system in which the ring atoms are each carbon.

As used herein the term aryl as a group or part of a group is intended to mean an aromatic hydrocarbon system, for example phenyl, naphthyl, phenanthrenyl, anthracenyl, pyrenyl, and the like, e.g., of 6-20, preferably 6-10 carbon atoms.

In some embodiments, aryl groups are a naphthyl or phenyl ring, respectively, each of which is optionally substituted by from 1 to 3 substituents selected from halogen, $C_1$-$C_6$ alkyl, phenyl, benzyl, O-phenyl, O-benzyl, —$SO_2NH_2$, —$SO_2NH$ ($C_1$-$C_6$ alkyl), —$SO_2N(C_1$-$C_6$ alkyl)$_2$, —$CH_2COOH$, —$CO_2H$, —$CO_2Me$, —$CO_2Et$, —$CO_2iPr$, —C(=O)$NH_2$, —C(=O)NH($C_1$-$C_6$), —C(=O)N($C_1$-$C_6)_2$, —OH, —S—$C_1$-$C_6$ alkyl, —O—$C_1$-$C_6$ alkyl, —$NO_2$, —$NH_2$, —$CF_3$, $OCF_3$, and CN.

As used herein, the term arylalkyl is intended to mean a group of formula -alkyl-aryl, wherein aryl and alkyl have the definitions above. In some embodiments, the arylalkyl group is a benzyl group that is optionally substituted by from 1 to 3 substituents selected from halogen, $C_{1-6}$ alkyl, phenyl, benzyl, Ophenyl, Obenzyl, $SO_2NH_2$, $SO_2NH(C_{1-6}$ alkyl), $SO_2N$ ($C_{1-6}$ alkyl)$_2$, $CH_2COOH$, $CO_2H$, $CO_2Me$, $CO_2Et$, $CO_2iPr$, C(=O)$NH_2$, C(=O)NH($C_{1-6}$), C(=O)N($C_{1-6})_2$, OH, $SC_{1-6}$ alkyl, $OC_{1-6}$ alkyl, $NO_2$, $NH_2$, $CF_3$, $OCF_3$ and CN.

As used herein, the term heterocyclo as a group or part of a group is intended to mean a mono- or bi-cyclic ring system that contains from one to three hetero (i.e., non-carbon) atoms selected from O, N and S and for example 3-20 ring atoms. Heterocyclo groups include fully saturated and partially saturated cyclic heteroatom-containing moieties (containing for example none, or one or more double bonds). Such fully and partially saturated cyclic non-aromatic groups are also collectively referred to herein as "heterocycloalkyl" groups. Hetorocyclo groups also include cyclic heteroatom-containing moieties that contain at least one aromatic ring. Such fully and partially aromatic moieties are also collectively referred to herein as "heteroaryl" groups. In some embodiments, heterocyclo groups are:

(a) a five-membered heterocyclic ring containing one to three ring heteroatoms selected from N, S or O exemplified by, but not limited to, furan, imidazole, imidazolidine, isothiazole, isoxazole, oxathiazole, oxazole, oxazoline, pyrazole, pyrazolidine, pyrazoline, pyrrole, pyrrolidine, pyrroline, thiazoline, or thiophene, the five-membered heterocyclic ring being optionally substituted by from 1 to 3 substituents selected from halogen, $C_{1-10}$ alkyl, preferably $C_{1-6}$ alkyl, $OC_{1-10}$ alkyl, preferably $OC_{1-6}$ alkyl, $NO_2$, $NH_2$, CN, $CF_3$, $CO_2H$; or (b) a six-membered heterocyclic ring containing one to three ring heteroatoms selected from N, S or O exemplified by, but not limited to morpholine, oxazine, piperazine, piperidine, pyran, pyrazine, pyridazine, pyridine, pyrimidine, thiadizine, or thiazine, the six-membered heterocyclic ring being optionally substituted by from 1 to 3 substituents selected from halogen, $C_{1-10}$ alkyl, $OC_{1-10}$ alkyl, CHO, $CO_2H$, C(=O)$R_{20}$, $SO_2R_{20}$, $NO_2$, $NH_2$, CN, $CF_3$ or OH; or (c) a bicyclic ring moiety optionally containing from 1 to 3 ring heteroatoms selected from N or O exemplified by, but not limited to, benzodioxine, benzodioxole, benzofuran, chromene, cinnoline, indazole, indole, indoline, indolizine, isoindole, isoindoline, isoquinoline, napthalene, napthyridine, phthalazine, purine, quinazoline, quinoline, or quinolizine, the bicyclic ring moiety being optionally substituted by from 1 to 3 substituents selected from halogen, $C_{1-6}$ alkyl, $OC_{1-6}$ alkyl, CHO, $NO_2$, $NH_2$, CN, $CF_3$, $CO_2H$, C(=O)$R_{20}$, $SO_2R_{20}$, or OH.

The compounds according to the invention can exist as pharmaceutically acceptable salts, including pharmaceutically acceptable acid addition salts prepared from pharmaceutically acceptable acids, including inorganic and organic acids. Such acids include acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like. Further representative examples of pharmaceutically acceptable salts can be found in, *Journal of Pharmaceutical Science*, 66, 2 (1977), incorporated herein by reference. Reacting compounds of this invention with one or more equivalents of an appropriately reactive base may also prepare basic salts. Both mono and polyanionic salts are contemplated, depending on the number of acidic hydrogens available for deprotonation. Appropriate bases can be either organic or inorganic in nature. For example, inorganic bases such as $NaHCO_3$, $Na_2CO_3$, $KHCO_3$, $K_2CO_3$, $Cs_2CO_3$, LiOH, NaOH, KOH, $NaH_2PO_4$, $Na_2HPO_4$, $Na_3PO_4$ as well as others are suitable. Organic bases including amines, alkyl amines, dialkyamines, trialylamines, various cyclic amines (such as pyrrolidine, piperidine, etc) as well as other organic amines are suitable. Quaternary ammonium alkyl salts may also prepared by reacting a compound of the invention with an appropriately reactive organic electrophile (such as methyl iodide or ethyl triflate). The compounds described herein can also be administered in the form of liposomes. As is known in the art, liposomes are generally derived from phospholipids or other lipid substances, and are formed by mono or multilamellar hydrated liquid crystals that are dispersed in an aqueous medium. Any nontoxic, pharmacologically acceptable lipid capable of forming liposomes can be used.

Liposome-containing compositions in accordance with the present invention can contain, in addition to the compound of Formula I, II or III, stabilizers, preservatives, excipients and the like. The preferred lipids include phospholipids, including phosphatidyl cholines (lecithins), both natural and synthetic. Methods for liposome formation are well known in the art, and will be apparent to the skilled artisan.

The present invention also includes compounds of Formulas I, II and III in prodrug form. In general, the inclusion of a physiologically labile group on a compound of the invention will result in the regeneration of the desired compound when exposed to gastric juice, plasma, or in any tissue or compartment where the appropriate endogenous enzymes or reactive substances are present. One non-limiting example of such a physiologially labile group includes an alkyl ester of the carboxylic acid of the compound of Formulas I or II. Such esters are known to undergo hydrolysis to the free acid either in the gut by gastric juice or in the plasma by various endogenous esterases. A further non-limiting example is replacement of the group X in Formula I or II with a group of formula O-G, where G is an alkyl group that is removed by metabolizing enzymes in the liver or gut, or with the moiety remaining after removal of the alpha carboxyl or amino group from a naturally occurring amino acid. Any such structure that imparts physiologically labile functionality is within the definition of prodrug as used herein.

The acid or base addition salts can be obtained as the direct products of compound synthesis. In the alternative, the free base can be dissolved in a suitable solvent containing the appropriate acid or base, and the salt isolated by evaporating the solvent or otherwise separating the salt and solvent. The compounds of this invention may form solvates with standard low molecular weight solvents using methods known to the skilled artisan.

Compositions of the invention may conveniently be administered in unit dosage form and can be prepared by any of the methods well known in the pharmaceutical art, for example, as described in *Remington's Pharmaceutical Sciences* (Mack Pub. Co., Easton, Pa., 1980).

The compounds of the invention can be employed as the sole active agent in a pharmaceutical or can be used in combination with other active ingredients, which could facilitate the therapeutic effect of the compound.

Compounds of the present invention or a solvate or physiologically functional derivative thereof can be used as active ingredients in pharmaceutical compositions, specifically as selectin inhibitors. The term "selectin inhibitor" is intended to mean a compound that interferes with (i.e., antagonizes) the normal physiological function of selectins in intercellular adhesion.

The term active ingredient in the context of pharmaceutical compositions of the invention is intended to mean a component of a pharmaceutical composition that provides the primary pharmaceutical benefit, as opposed to an inactive ingredient which would generally be recognized as providing no pharmaceutical benefit. The term pharmaceutical composition is intended to mean a composition comprising at least one active ingredient and at least one ingredient that is not an active ingredient (for example and not limitation, a filler, dye, or a mechanism for slow release), whereby the composition is amenable to use for a specified, efficacious outcome in a mammal (for example, and not limitation, a human).

The compounds of Formulas I, II and III are useful for the treatment or prophylaxis multiple disorders in mammals, including, but not limited to, human. Compounds of the present invention can be administered by oral, sublingual, parenteral, rectal, topical administration or by a transdermal patch. Transdermal patches dispense a drug at a controlled rate by presenting the drug for absorption in an efficient manner with a minimum of degradation of the drug. Typically, transdermal patches comprise an impermeable backing layer, a single pressure sensitive adhesive and a removable protective layer with a release liner. One of ordinary skill in the art will understand and appreciate the techniques appropriate for manufacturing a desired efficacious transdermal patch based upon the needs of the artisan.

Different amounts of the compounds of the present invention will be required to achieve the desired biological effect. The amount will depend on factors such as the specific compound, the use for which it is intended, the means of administration, and the condition of the treated individual and all of these dosing parameters are within the level of one of ordinary skill in the medicinal arts. A typical dose can be expected to fall in the range of 0.001 to 200 mg per kilogram of body weight of the mammal. Unit doses may contain from 1 to 200 mg of the compounds of the present invention and can be administered one or more times a day, individually or in multiples.

Pharmaceutical compositions, including at least one compound disclosed herein, and/or a pharmacologically acceptable salt or solvate thereof can be employed as an active ingredient combined with one or more carriers or excipients. Such compositions can be used in the treatment of clinical conditions for which a selectin inhibitor is indicated. The active ingredient or ingredients can be combined with the carrier in either solid or liquid form in a unit dose formulation. Formulations can be prepared by any suitable method, typically by uniformly mixing the active compound(s) with liquids or finely divided solid carriers, or both, in the required proportions, and then, if necessary, forming the resulting mixture into a desired shape.

Conventional excipients, such as binding agents, fillers, acceptable wetting agents, tabletting lubricants, and disintegrants can be used in tablets and capsules for oral administration. Liquid preparations for oral administration can be in the form of solutions, emulsions, aqueous or oily suspensions, and syrups. Alternatively, the oral preparations can be in the form of dry powder that can be reconstituted with water or another suitable liquid vehicle before use. Additional additives such as suspending or emulsifying agents, non-aqueous vehicles (including edible oils), preservatives, and flavorings and colorants can be added to the liquid preparations. Parenteral dosage forms can be prepared by dissolving the compound of the invention in a suitable liquid vehicle and filter sterilizing the solution before filling and sealing an appropriate vial or ampoule. These are just a few examples of the many appropriate methods well known in the art for preparing dosage forms.

It is noted that when the selectin inhibitors are utilized as active ingredients in a pharmaceutical composition, these are not intended for use only in humans, but in non-human mammals as well. Those of ordinary skill in the art are readily credited with understanding the utility of such compounds in such settings.

This invention also provides a process for preparing a compound of formula I which comprises one of the following:

a) reacting a compound of formula

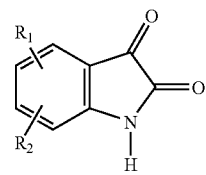

wherein $R_1$ and $R_2$ are as defined in claim 1, with a compound of formula:

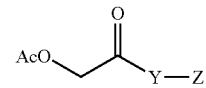

wherein Ac is acetyl and Y and Z are as defined in claim 1 to give a corresponding compound of formula I wherein L is $CO_2H$ in the 4 position and X is OH in the 3 position; or b) converting a compound of formula I to a pharmaceutically acceptable salt thereof or vice versa.

The compounds of the present invention can be readily prepared according to a variety of synthetic regimes, all of which would be familiar to one skilled in the art. A representative general synthesis is set forth below in Scheme 1.

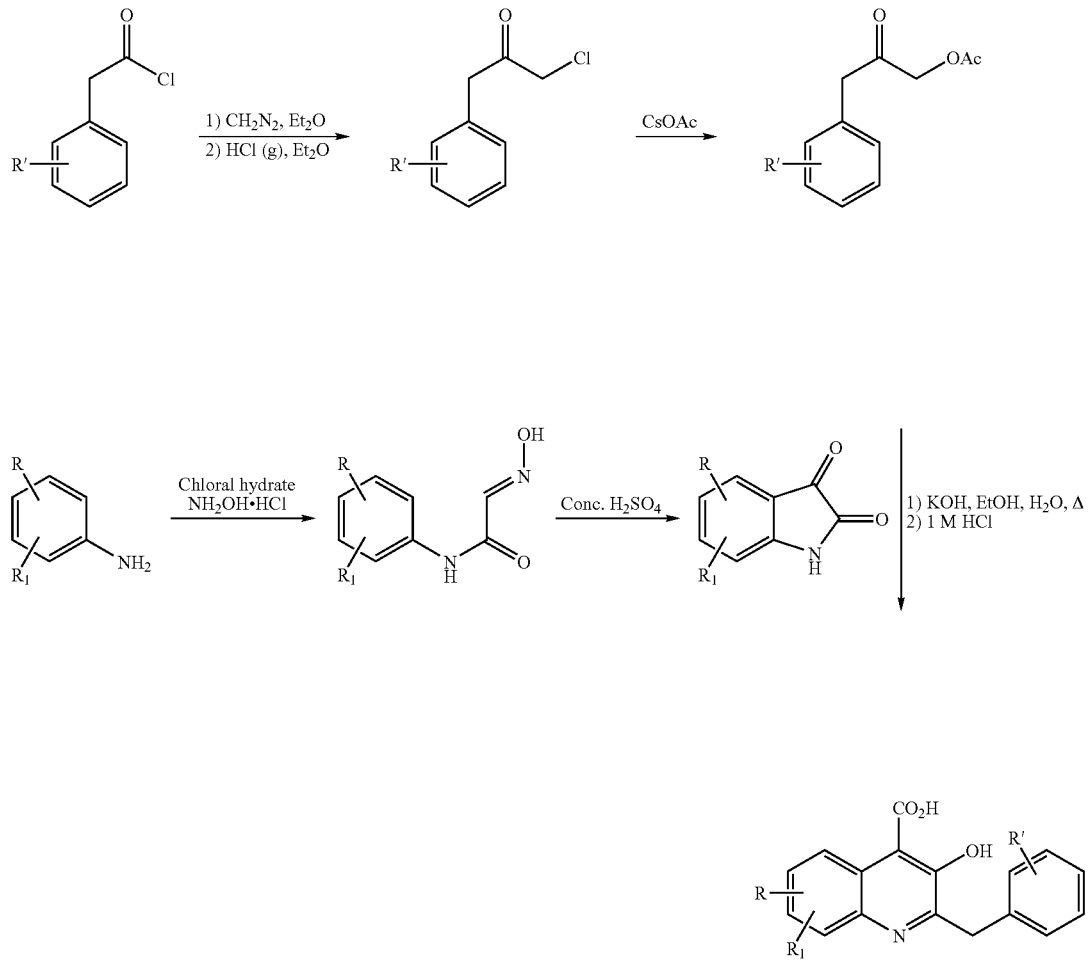

Scheme 1
General synthetic scheme for the preparation of compounds of Formula I

Those of skill in the art will appreciate that a wide variety of compounds of the invention can be prepared according to Scheme I. For example, by starting with an appropriately substituted phenacetyl chloride one could prepare numerous differently substituted benzyl groups at the quinoline 2-position. Likewise, those skilled in the art also will recognize that variously substituted anilines can be purchased or prepared and used for the construction of correspondingly substituted quinolines. Additionally, protection of the carboxylic acid, for example via esterification, or another masking reaction, allows for selective alkylation or functionalization of the 3-hydroxy group located on the quinoline ring.

In the synthesis of many compounds described herein, protecting groups can be employed to protect various functionality or functionalities during the synthesis. Representative protecting groups suitable for a wide variety of synthetic transformations are disclosed in Greene and Wuts, *Protective Groups in Organic Synthesis,* 2d ed, John Wiley & Sons, New York, 1991, the disclosure of which is incorporated herein by reference in its entirety.

While the present invention has been described with specificity in accordance with certain of its preferred embodiments, the following examples serve only to illustrate the invention and are not intended to limit the same.

EXAMPLES

Synthesis of Compounds

The compounds of Formula I can be prepared as described herein by following the general synthetic approach outlined in Scheme 1, using commercially available starting materials.

Example 1

Preparation of 2-(4-Chloro-Benzyl)-3-Hydroxy-7,8,-Dimethyl-Quinoline-4-Carboxylic Acid (Compound 1)

2-(4-Chloro-benzyl)-3-hydroxy-7,8,-dimethyl-quinoline-4-carboxylic acid was prepared according to Scheme 2 below.

Scheme 2
Preparation of 2-(4-Chloro-benzyl)-3-hydroxy-7,8,-dimethyl-quinoline-4-carboxylic acid
(Compound 1)

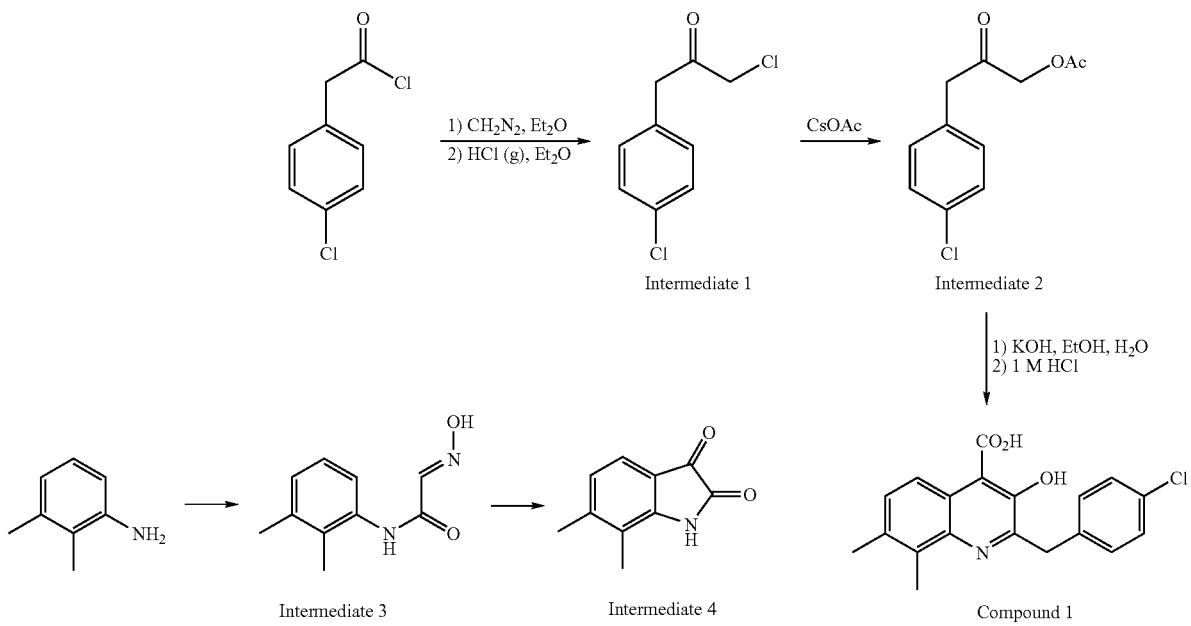

Intermediate 1:
1-Chloro-3-(4-chloro-phenyl)-propan-2-one

A solution of 30 g (158.7 mmol) of p-chlorophenacyl chloride in 200 ml of ether was added over 30 min to 420 ml of diazomethane in ether (0.57 mmol/ml) while stirring in an ice bath. [Diazomethane was prepared using the procedure described in Org. Syn. Coll. Vol. II pages 165-167]. The reaction was stirred in ice for 3 h, then overnight at room temperature. Next, a gentle stream of anhydrous HCl gas was passed through the solution of the diazoketone at 0-4° C. for ca. 5-8 min, till the evolution of nitrogen ceased. After an additional hour in the ice bath, the reaction was poured into 700 ml crushed ice-water. The mixture was stirred 15 min. diluted with 400 ml ether and the organic phase was washed with 750 ml of a 5% sodium carbonate solution, then 500 ml semi-saturated brine. The combined organic layers dried (sodium sulphate) ether solutions were evaporated to yield 25.5 g of crude intermediate 1 as a pale yellow solid.

A solution of the crude was dissolved in 30-35 ml of methylene chloride was purified by flash chromatography on 500 g silica gel 60 (Merck 0.04-0.063 mm). Elution of the column (40×6 cm) with ethyl acetate-hexanes 20:80 gave 21.1 g (65.3% yield) of the pure intermediate 1 as colorless crystals. $^1$H NMR (CDCl$_3$, 300 MHz), δ ppm 3.88 (s, 2H) 4.11 (s, 2H) 7.16 (d, J=8.59 Hz, 2H) 7.32 (d, J=8.59 Hz, 2H).

Intermediate 2: Acetic Acid
3-(4-chloro-phenyl)-2-oxo-propyl Ester

To a gently refluxing solution of 21.1 g (103.9 mmol) of intermediate 1 in 200 ml ethanol was added in one portion 21.94 g (114.3 mmol, 1.1 equiv.) cesium acetate in 100 ml water and 10 ml glacial acetic acid. After refluxing for 3H the reaction reached an optimal stage (TLC: ethyl acetate:hexanes 20:80, ammonium molybdate spray). Most of the ethanol was removed by evaporation and the resulting oily mixture was distributed between 2×800 ml portions of ethyl acetate and 2×500 ml ice cold semi saturated sodium bicarbonate solution. The organic layers were washed in sequence with 500 ml brine, dried sodium sulfate, and evaporated in vacuo. A solution of the residue in 30 ml methylene chloride was purified by flash chromatography on 500 g silica gel. Elution of the column with ethyl acetate:hexanes 20:80 to 30:70 afforded 12.09 g (51.3%) of the intermediate 2 as a colorless crystalline solid. Recrystallization from ether:hexanes provided 11.7 g of pure intermediate 2. 1.88 g of starting material was also recovered. $^1$H NMR (CDCl$_3$, 300 MHz), δ ppm 2.16 (s, 3H) 3.72 (s, 2H) 4.69 (s, 2H) 7.15 (d, J=8.59 Hz, 2H) 7.31 (d, J=8.59 Hz, 2H).

Intermediate 3:
N-(2,3-Dimethyl-phenyl)-2-hydroxyimino-acetamide

This compound was prepared via the isatin synthesis described by Rewcastle et al. *J. Med. Chem.,* 1991, 34, 217. Chloral hydrate (45 g, 0.27 mol), hydroxylamine hydrochloride (205 g, 1.25 mol) and sodium sulfate (226.5 g, 1.6 mol) were placed in a 2 L round-bottomed flask, and 750 mL water were added. To this suspension was added 2,3-dimethyl aniline (29.05 g, 0.24 mol) in 250 mL water containing concentrated HCl (25 mL). The suspension was heated to 45° C. under N$_2$ in 90 min, then to 52° C. over 45 min, and finally to 75° C. for 60 min. The reaction mixture was cooled to room temperature. The precipitate was collected by filtration, washing with water, petroleum ether and dried overnight in a vacuum dessicator to give crude isonitroso intermediate 3 (40.1 g, 87%).

Intermediate 4: 6,7-Dimethyl-1H-indole-2,3-dione

Intermediate 3 (20 g, 0.1 mol) was added in small portions, with stirring, to 80 mL CH$_3$SO$_3$H at 70° C.-80° C. in one hour. After the addition was complete it was left at the same temperature for 15 more minutes and was then poured onto crushed ice in a beaker. Additional ice was added until the outside of the beaker felt cold to the touch. The precipitate was then collected and dissolved in 1N aqueous NaOH. Neutralization with acetic acid precipitated impurities which were removed by filtration, and acidification (HCl) of the filtrate gave isatin intermediate 4 as a solid (12.8 g, 70%). $^1$H NMR (400 MHz, DMSO-D6) δ ppm 2.09 (s, 3H) 2.27 (s, 3H) 6.89 (d, J=7.58 Hz, 1H) 7.25 (d, J=7.58 Hz, 1H) 11.02 (s, 1H).

2-(4-Chloro-benzyl)-3-hydroxy-7,8,-dimethyl-quinoline-4-carboxylic Acid (Compound 1)

Intermediate 4 (8.00 g, 45.67 mMol) was added in one portion to 70 mL 6N KOH at 100-2° C. and the dark suspension was stirred till a clear, yellow solutions was obtained.

An excess of intermediate 2 (18.63 g, 82.20 mMol, 1.8 equiv.) in 140 mL lukewarm EtOH was then added in small portions over 1.5 h, while stirring and heating at 100-2° C. The reaction was gently refluxed 1.5 h longer, cooled to room temperature, and diluted slowly with 400 mL H$_2$O under vigorous magnetic stirring. The resulting turbid solution was acidified by very slow, dropwise addition of 2.4N HCl. A brown-red gum which formed at pH~12 was removed by decantation/filtration. Further slow acidification of the filtrate under vigorous magnetic stirring eventually produced a permanent yellow precipitate. At pH ~6.5 to 6 some gummy precipitate started impairing the stirring. Addition of a few drops of 6N KOH dissolved the gum and the yellow solid was separated by filtration and washed with 150 mL water. Further acidification of the filtrate to pH 0 yielded at first only gummy byproducts, then some unreacted 6.7-dimethylisatin. The solid obtained at pH~6.5 was suspended in 200 mL 1N HCl, stirred overnight at room temperature, collected by filtration, washed with several small portions of water, and partially dried by suction. The remaining water was removed by azeotropic evaporation under reduced pressure with 3 400 mL portions of MeCN. The residue was stirred overnight with 800 mL MeCN, filtered, and dried in high vacuo to give 8.00 g (51.2%) of Compound 1 as a canary yellow solid. $^1$H NMR (400 MHz, DMSO-d$_6$) δ ppm 2.40 (s, 3H) 2.61 (s, 3H) 4.33 (s, 2H) 7.30-7.37 (m, 4H) 7.39 (d, J=8.55 Hz, 1H) 8.21 (d, J=8.54 Hz, 1H).

Example 2

Preparation of 2-(4-Chloro-Benzyl)-3-Hydroxy-8-Phenyl-Quinoline-4-Carboxylic Acid (Compound 2)

2-(4-Chloro-benzyl)-3-hydroxy-8-phenyl-quinoline-4-carboxylic acid was prepared according to Scheme 3 below.

Scheme 3
Preparation of 2-(4-Chloro-benzyl)-3-hydroxy-8-phenyl-quinoline-4-carboxylic acid (Compound 2)

Intermediate 5: 2-Hydroxyimino-N-(2-iodo-phenyl)-acetamide

Intermediate 5 was prepared according to the method described by Yang et al. (*J. Am. Chem. Soc.*, 1996, 118, 9557), and the cyclization to the isatin was carried out as described by Marvel and Hiers (*Org. Synth. Coll. Vol. I*, 327). Hydroxylamine hydrochloride (11.4 g, 0.165 mol) and sodium sulfate (52 g, 0.366 mol) were placed in a 1 L round-bottomed flask, and 310 mL water, 16 mL 2 M aqueous hydrochloric acid and 2-iodoaniline (Aldrich, 10 g, 46 mmol) were added. Chloral hydrate (9.1 g, 55 mmol) was then added, and the mixture was heated at 55° C. overnight, with stirring. After cooling to room temperature, the slightly lumpy precipitate was collected by filtration, washing once with water, and dried under vacuum to yield isonitroso intermediate 5 as a beige solid (11.0 g, 83% yield): $^1$H NMR (400 MHz, DMSO-D$_6$) δ ppm 6.99 (t, J=7.71 Hz, 1H) 7.41 (t, 1H) 7.63 (s, 1H) 7.76 (dd, J=8.08, 1.26 Hz, 1H) 7.90 (dd, J=7.83, 1.26 Hz, 1H) 9.38 (s, 1H) 12.42 (s, 1H).

Intermediate 6: 7-Iodo-1H-indole-2,3-dione

To carry out the cyclization step, intermediate 5 (11.0 g, 38.0 mmol) was added in small portions, with stirring, to 30 mL concentrated sulfuric acid which had been heated to 55° C. in a 125 mL Erlenmeyer flask. The temperature of the solution was maintained below 70° C. until all the isonitroso had been added, and then increased to 80° C. for an additional 10 minutes. The dark-colored solution was then cooled to room temperature, poured onto 150 mL crushed ice, and allowed to stand for 10 minutes. The precipitate was collected by filtration, washing three times with water, and dried under vacuum to yield isatin 6 as a dark red powder of sufficient purity to be used in the next step (8.30 g, 80% yield, 66% yield from 2-iodoaniline): $^1$H NMR (400 MHz, DMSO-D$_6$) δ ppm 6.89 (t, J=7.71 Hz, 1H) 7.50 (d, J=7.33 Hz, 1H) 7.95 (d, J=6.82 Hz, 1H) 11.01 (s, 1H).

Intermediate 7: 7-Phenyl-1H-indole-2,3-dione

This compound was prepared according to the procedure described by Lisowski et al. *J. Org. Chem.*, 2000, 65, 4193. To a 1 L 3-necked round-bottomed flask fitted with a reflux condenser were added intermediate 6 (2.0 g, 7.33 mmol) and tetrakis[triphenylphosphine]palladium (0.424 g, 0.367 mmol), followed by 225 mL 1,2-dimethoxyethane. The atmosphere in the reaction vessel was made inert by opening to vacuum, then to a positive pressure of nitrogen (3×). Phenylboronic acid (Aldrich, 0.983 g, 8.06 mmol) and a solution of sodium bicarbonate (1.23 g, 14.7 mmol) in 225 mL water were added, and the evacuation/nitrogen procedure repeated one more time. The reaction mixture was then refluxed until t.l.c. (10% ethyl acetate in dichloromethane) showed complete disappearance of 7-iodoisatin (1-2 hours). After cooling to room temperature, the 1,2-dimethoxyethane was removed under reduced pressure. The residue was diluted with 1M aqueous hydrochloric acid and extracted into ethyl acetate (3×). The organic layer was washed with brine, dried over anhydrous magnesium sulfate, filtered, and evaporated under reduced pressure to give crude 7-phenylisatin 7.

The procedure described above was repeated 8 more times. The combined crude product was purified by flash chromatography over silica gel, eluting with 1% ethyl acetate in dichloromethane, to give pure phenylisatin 7 as orange needlelike crystals (10.94 g, 74% yield from 18 g 7-iodoisatin): $^1$H NMR (400 MHz, DMSO-D$_6$) δ ppm 7.18 (t, J=7.58 Hz, 1H) 7.48 (m, 6H) 7.59 (d, J=8.84 Hz, 1H) 10.91 (s, 1H).

2-(4-Chloro-benzyl)-3-hydroxy-8-phenyl-quinoline-4-carboxylic Acid (Compound 2)

This compound was prepared by the procedure described by Cragoe et al. *J. Org. Chem.*, 1953, 18, 561. In a 50 mL 2-necked round-bottomed flask fitted with a reflux condenser, 7-phenylisatin 7 (0.79 g, 3.5 mmol) was suspended in 4 mL 6 M aqueous potassium hydroxide and heated to 100° C. A solution of intermediate 2 (1.00 g, 4.41 mmol) in 4 mL warm ethanol was then added by syringe in small portions over the course of 1 hour. After the addition had been completed, the reaction mixture was refluxed for 4 additional hours. It was then cooled to room temperature, and ethanol was removed under reduced pressure. The residue was diluted with 20 mL water, chilled for ½ hour and filtered, and the filtrate acidified to pH 1 with 1M aqueous hydrochloric acid. The precipitate of crude acid was collected by filtration, purified by silica gel chromatography (gravity column, eluting with 70 ethyl acetate: 5 acetonitrile: 2.5 methanol: 2.5 water [+0.5% triethylamine]) and lyophilized to give pure product as the triethylammonium salt. The salt was then dissolved in 20% acetonitrile in water and the solution acidified with concentrated hydrochloric acid and extracted into ethyl acetate (3×). This ethyl acetate solution was washed with brine, dried over anhydrous magnesium sulfate, filtered, evaporated, and lyophilized to give pure acid Compound 2 as a fluffy, bright yellow solid (0.149 g, 11% yield): $^1$H NMR (400 MHz, DMSO-D$_6$) δ 4.23 (s, 2H) 7.27 (m, 2H) 7.32 (m, 2H) 7.37 (m, 3H) 7.52 (m, 2H) 7.56 (dd, J=7.3, 1.5 Hz, 1H) 7.63 (m, 1H) 8.46 (dd, J=8.3, 1.5 Hz, 1H). Anal. Calcd for $C_{23}H_{16}ClNO_3$: C, 70.86; H, 4.14; N, 3.67. Found: C, 70.58; H, 4.33; N, 3.43.

Example 3

Preparation of 2-(4-Chloro-Benzyl)-3-Hydroxy-8-Trifluoromethyl-Quinoline-4-Carboxylic Acid (Compound 3)

The preparation of this compound is shown in Scheme 4, below.

Scheme 4
Preparation of 2-(4-Chloro-benzyl)-3-hydroxy-8-trifluoromethyl-quinoline-4-carboxylic acid (Compound 3)

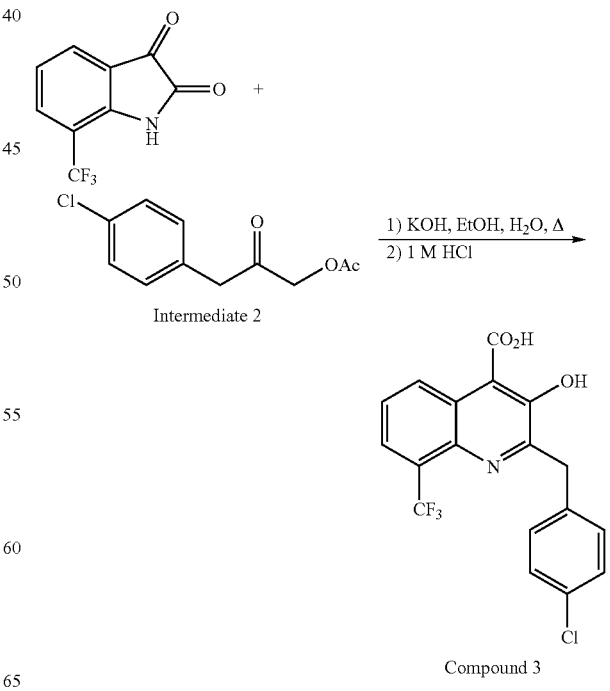

2-(4-Chloro-Benzyl)-3-Hydroxy-8-Trifluoromethyl-Quinoline-4-Carboxylic Acid (Compound 3)

This compound was synthesized by the procedure described above for Compound 2, reacting commercially available isatin, 7-trifluoromethyl-1H-indole-2,3-dione (1.00 g, 4.31 mmol) with 3-(4-chlorophenyl)-2-oxopropyl acetate (intermediate 2, 1.22 g, 5.38 mmol). Acidification during reaction work-up did not yield a solid precipitate, so the crude acid was obtained by extraction into ethyl acetate (3×)—the ethyl acetate solution was washed with brine, dried over anhydrous magnesium sulfate, filtered and evaporated. The crude product was purified by flash chromatography over silica gel, eluting with 70 ethyl acetate: 5 acetonitrile: 2.5 methanol: 2.5 water (+0.5% triethylamine), and lyophilized to yield the pure triethylammonium salt. To convert the salt back to the free acid form, it was taken up in 1:1 acetonitrile/water, acidified with concentrated hydrochloric acid, and then diluted with additional water to 20% acetonitrile in water. The acid precipitated and was collected by filtration and dried under vacuum to yield pure product Compound 3 as an off-white powder (0.695 g, 42% yield): $^1$H NMR (400 MHz, DMSO-D$_6$) δ 4.32 (s, 2H) 7.34 (m, 4H) 7.68 (t, 1H) 7.94 (d, J=7.3 Hz, 1H) 8.83 (d, J=8.6 Hz, 1H). Anal. Calcd for C$_{18}$H$_{11}$ClF$_3$NO$_3$: C, 56.64; H, 2.90; N, 3.67. Found: C, 56.47; H, 2.73; N, 3.53.

Example 4

Preparation of 2-(4-Chloro-Benzyl)-3-Hydroxy-8-Trifluoromethoxy-Quinoline-4 Carboxylic Acid (Compound 4)

The preparation of this compound is shown in Scheme 5, below.

Scheme 5
Preparation of 2-(4-Chloro-benzyl)-3-hydroxy-8-trifluoromethoxy-quinoline-4-carboxylic acid (Compound 4)

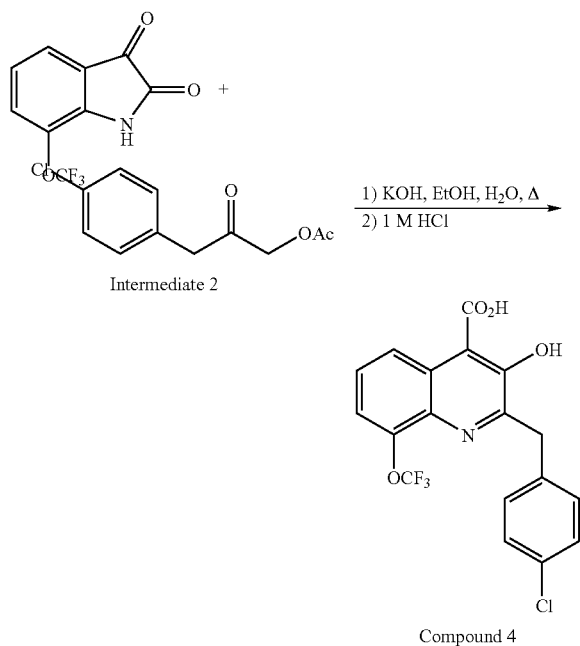

Compound 4

2-(4-Chloro-benzyl)-3-hydroxy-8-trifluoromethoxy-quinoline-4-carboxylic acid (Compound 4)

This compound was synthesized and purified by the procedures described above for Compound 3, reacting isatin (7-trifluoromethoxy-1H-indole-2,3-dione, 1.00 g, 4.03 mmol) with intermediate 2 (1.14 g, 5.04 mmol). Pure product was obtained as an ivory powder (Compound 4), 0.264 g, 16% yield): $^1$H NMR (400 MHz, DMSO-D$_6$) δ 4.33 (s, 2H) 7.33 (m, 4H) 7.56 (d, J=7.8 Hz, 1H) 7.61 (t, 1H) 8.57 (dd, J=8.5, 1.4 Hz, 1H). Anal. Calcd for C$_{18}$H$_{11}$ClF$_3$NO$_4$: C, 54.36; H, 2.79; N, 3.52. Found: C, 54.12; H, 2.75; N, 3.33.

Example 5

Preparation of 2-(4-Chlorobenzyl)-3-Hydroxy-8-Isopropylquinoline-4-Carboxylic Acid (Compound 5)

This compound is prepared according to Scheme 6, below.

Scheme 6
Preparation of 2-(4-chlorobenzyl)-3-hydroxy-8-isopropylquinoline-4-carboxylic acid (Compound 5)

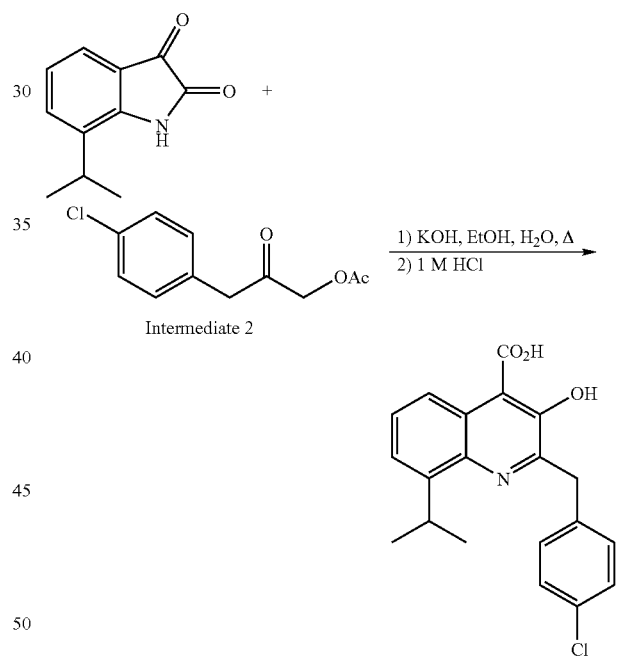

Compound 5

2-(4-chlorobenzyl)-3-hydroxy-8-isopropylquinoline-4-carboxylic Acid (Compound 5)

This compound was synthesized and purified by the procedures described above for Compound 3, reacting isatin (7-isopropyl-1H-indole-2,3-dione, 1.00 g, 4.85 mmol) with intermediate 2 (1.37 g, 6.06 mmol). The free acid obtained after chromatography and hydrochloric acid treatment was recrystallized from acetonitrile to give pure product, Compound 5, as a yellow powder (0.228 g, 13% yield): $^1$H NMR (400 MHz, DMSO-D$_6$) δ 1.25 (d, J=7.1 Hz, 6H) 4.11 (septet, 1H) 4.33 (s, 2H) 7.34 (s, 4H) 7.43 (dd, J=7.3, 1.0 Hz, 1H) 7.51

(m, 1H) 8.26 (dd, J=8.5, 1.4 Hz, 1H). Anal. Calcd for $C_{20}H_{18}ClNO_3$: C, 67.51; H, 5.10; N, 3.94. Found: C67.22; H, 4.99; N, 3.89.

Example 6

Preparation of 2-(4-Chlorobenzyl)-3-Hydroxy-8-Methylquinoline-4-Carboxylic Acid (Compound 6)

This compound was prepared according to Scheme 7, below.

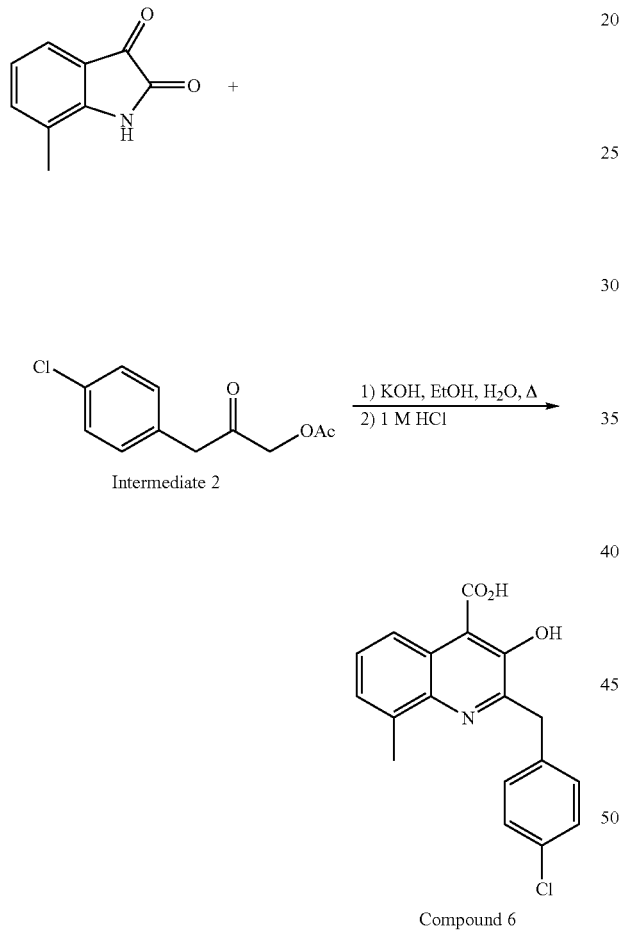

Scheme 7
Preparation of 2-(4-chlorobenzyl)-3-hydroxy-8-methylquinoline-4-carboxylic acid (Compound 6)

Compound 6

2-(4-chlorobenzyl)-3-hydroxy-8-methylquinoline-4-carboxylic Acid (Compound 6)

This compound was synthesized by the procedure described above for Compound 2, reacting 7-methyl-1H-indole-2,3-dione (1.00 g, 6.21 mmol) with intermediate 2 (1.76 g, 7.76 mmol). The crude acid was purified as described above for Compound 3 to give Compound 6 as a bright yellow powder (0.774 g, 38% yield): $^1$H NMR (400 MHz, DMSO-$D_6$) δ 2.65 (s, 3H) 4.33 (s, 2H) 7.35 (m, 4H) 7.44 (m, 2H) 8.30 (dd, J=8.1, 1.3 Hz, 1H).

Example 7

Preparation of 2-(4-Chlorobenzyl)-8-Ethyl-3-Hydroxyquinoline-4-Carboxylic Acid (Compound 7)

This compound was prepared according to Scheme 8 below.

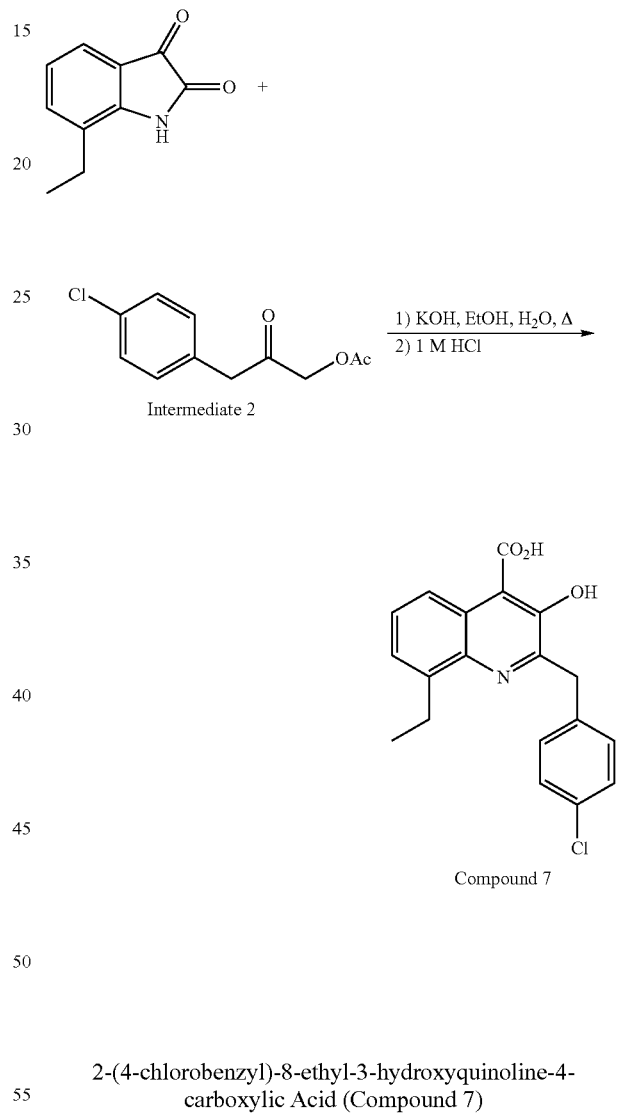

Scheme 8
Preparation of 2-(4-chlorobenzyl)-8-ethyl-3-hydroxyquinoline-4-carboxylic acid (Compound 7)

Compound 7

2-(4-chlorobenzyl)-8-ethyl-3-hydroxyquinoline-4-carboxylic Acid (Compound 7)

This compound was synthesized by the procedure described above for Compound 2, reacting 7-ethyl-1H-indole-2,3-dione (1.00 g, 5.71 mmol) with intermediate 2 (1.62 g, 7.14 mmol). The crude acid was purified as described above for Compound 3 to give product as a bright yellow powder (Compound 7, 0.488 g, 25% yield): $^1$H NMR (400 MHz, DMSO-$D_6$) δ 1.21 (t, J=7.5 Hz, 3H) 3.11 (q, J=7.3 Hz, 2H) 4.32 (s, 2H) 7.34 (s, 4H) 7.40 (d, J=7.1 Hz, 1H) 7.46 (t, 1H) 8.32 (d, J=8.1 Hz, 1H); HRMS (ESI+) calcd for $C_{19}H_{17}ClNO_3$ (MH$^+$) 342.0892, found 342.0890.

Example 8

Preparation of 7-Thiophen-3-yl-1H-Indole-2,3-Dione

This compound was prepared according to Scheme 9 below

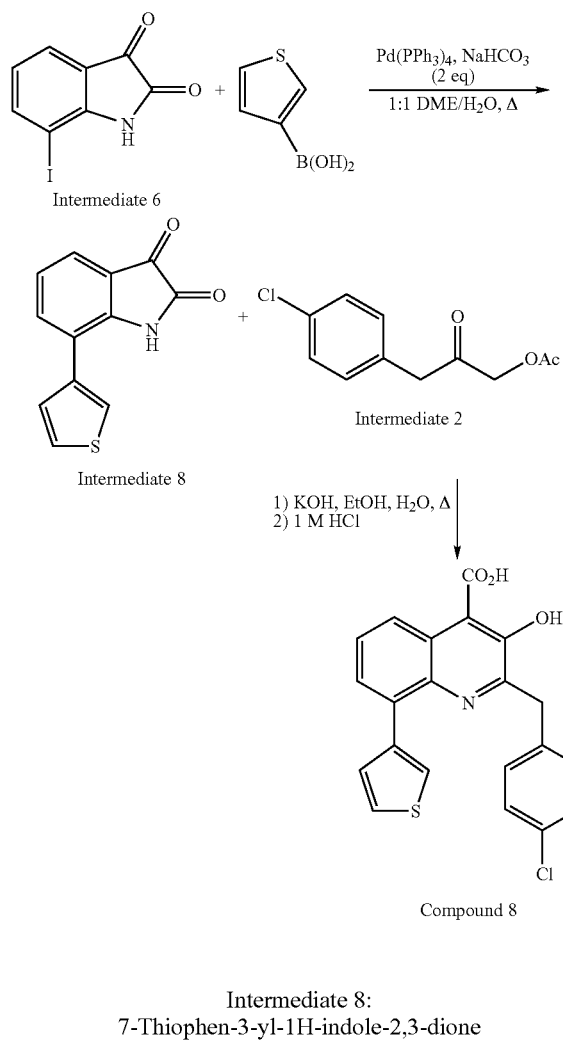

Intermediate 8: 7-Thiophen-3-yl-1H-indole-2,3-dione

This compound was prepared according to the procedure described by Lisowski et al. *J. Org. Chem.*, 2000, 65, 4193. To a 1 L 3-necked round-bottomed flask fitted with a reflux condenser were added intermediate 6 (2.0 g, 7.3 mmol) and tetrakis[triphenylphosphine]palladium (0.424 g, 0.367 mmol), followed by 115 mL ethylene glycol dimethyl ether. The atmosphere in the reaction vessel was made inert by opening to vacuum, then to a positive pressure of nitrogen (3×). Next, 3-thiopheneboronic acid (Aldrich, 1.03 g, 8.06 mmol) and a solution of sodium bicarbonate (1.23 g, 14.7 mmol) in 115 mL water were added, and the evacuation/nitrogen procedure repeated one more time. The reaction mixture was then refluxed until t.l.c. (10% ethyl acetate in dichloromethane) showed complete disappearance of 7-iodoisatin, 6, (1-3 hours). After cooling to room temperature, the organic solvent was removed under reduced pressure. The residue was diluted with 1M aqueous hydrochloric acid and extracted into ethyl acetate (3×). The organic layer was washed with brine, dried over anhydrous magnesium sulfate, filtered, and evaporated under reduced pressure. The crude product was purified by flash chromatography over silica gel, eluting with 3% ethyl acetate in dichloromethane, to give 7-(thien-3-yl)isatin, Intermediate 8, as a bright red crystalline material (0.91 g, 54% yield): $^1$H NMR (400 MHz, DMSO-D$_6$) δ 7.15 (t, 1H) 7.36 (dd, J=4.9, 1.4 Hz, 1H) 7.50 (dt, J=7.3, 1.0 Hz, 1H) 7.68 (d, J=1.5 Hz, 1H) 7.71 (m, 2H) 7.75 (dd, J=2.9, 1.4 Hz, 1H) 10.86 (s, 1H).

2-(4-chlorobenzyl)-3-hydroxy-8-(thien-3-yl)quinoline-4-carboxylic Acid (Compound 8)

This compound was synthesized by the procedure described above for Example 2, reacting intermediate 8 (0.91 g, 3.97 mmol) with intermediate 2 (1.12 g, 4.96 mmol). The crude acid was purified as described above for Compound 3 to give product as a bright yellow powder (Compound 8, 0.582 g, 37% yield): $^1$H NMR (400 MHz, DMSO-D$_6$) δ 4.34 (s, 2H) 7.36 (dd, 4H) 7.47 (dd, J=5.1, 3.0 Hz, 1H) 7.54 (m, 1H) 7.58 (m, 1H) 7.79 (m, 2H) 8.36 (dd, J=8.5, 1.1 Hz, 1H); HRMS (ESI/FTMS) calcd for C$_{21}$H$_{15}$ClNO$_3$S (MH$^+$) 396.0456, found 396.0459.

Example 9

Preparation of 8-Bromo-2-(4-Chlorobenzyl)-3-Hydroxyquinoline-4-Carboxylic Acid (Compound 9)

This compound was prepared according to Scheme 10 below.

Scheme 10
Preparation of 8-bromo-2-(4-chlorobenzyl)-3-hydroxyquinoline-4-carboxylic acid (Compound 9)

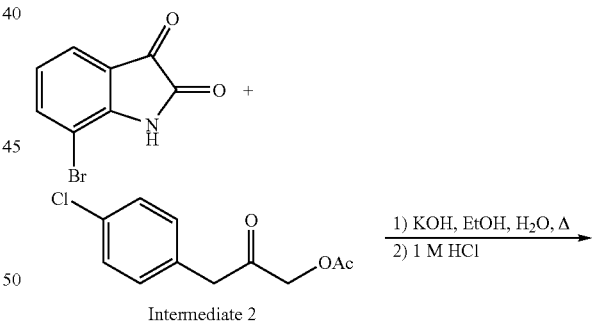

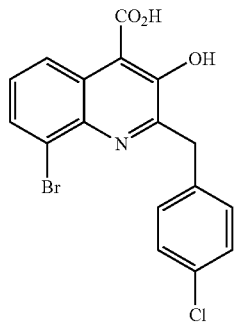

Compound 9

8-bromo-2-(4-chlorobenzyl)-3-hydroxyquinoline-4-carboxylic Acid (Compound 9)

This compound was synthesized by the procedure described above for Compound 2, reacting 7-Bromo-1H-indole-2,3-dione (1.00 g, 4.42 mmol) with intermediate 2 (1.25 g, 5.53 mmol). The crude acid was purified as described above for Compound 3, then recrystallized from acetonitrile to give product as large, bright yellow crystals (Compound 9, 0.398 g, 23% yield): $^1$H NMR (400 MHz, DMSO-D$_6$) δ 4.35 (s, 2H) 7.35 (m, 4H) 7.46 (dd, J=8.6, 7.6 Hz, 1H) 7.92 (dd, J=7.5, 1.1 Hz, 1H) 8.50 (dd, J=8.6, 1.3 Hz, 1H); HRMS (ESI/FTMS) calcd for C$_{17}$H$_{12}$BrClNO$_3$ (MH$^+$) 391.9684, found 391.9689. Anal. Calcd for C$_{17}$H$_{11}$BrClNO$_3$: C, 52.00; H, 2.82; N, 3.57. Found: C, 51.72; H, 2.77; N, 3.53.

Example 10

Preparation of 8-(Sec-Butyl)-2-(4-Chlorobenzyl)-3-Hydroxyquinoline-4-Carboxylic Acid (Compound 10)

This compound was prepared according to Scheme 11 below.

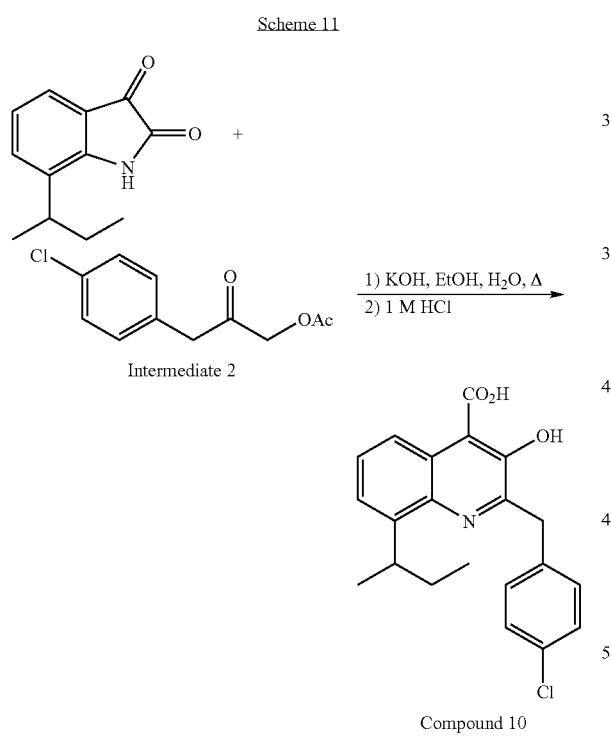

Scheme 11

Compound 10

8-(sec-butyl)-2-(4-chlorobenzyl)-3-hydroxyquinoline-4-carboxylic Acid (Compound 10)

This compound was synthesized by the procedure described above for Compound 2, reacting 7-sec-butylisatin (1.00 g, 4.92 mmol) with 3-(4-chlorophenyl)-2-oxopropyl acetate (1.39 g, 6.15 mmol). The crude acid was purified as described above for Compound 3 and, after hydrochloric acid treatment of an acetonitrile/water solution of the triethylammonium salt, extracted into ethyl acetate (3×), washed with brine, dried over anhydrous magnesium sulfate, filtered, evaporated and lyophilized. It was then purified (preparative HPLC, eluting with acetonitrile/water/triethylamine), and converted back to the free acid and extracted and evaporated once more as described above. A final lyophilization step gave product Compound 10 as a fluffy, bright yellow solid (72 mg, 3.9% yield): $^1$H NMR (400 MHz, DMSO-D$_6$) δ 0.74 (t, J=7.3 Hz, 3H) 1.22 (d, J=6.8 Hz, 3H) 1.61 (m, 2H) 3.91 (m, 1H) 4.32 (dd, 2H) 7.34 (m, 4H) 7.39 (d, J=6.1 Hz, 1H) 7.51 (dd, J=8.6, 7.3 Hz, 1H) 8.25 (dd, J=8.3, 1.3 Hz, 1H); HRMS (ESI/FTMS) calcd for C$_{21}$H$_{21}$ClNO$_3$ (MH$^+$) 370.1205, found 370.1204. Anal. Calcd for C$_{21}$H$_{20}$ClNO$_3$: C, 68.20; H, 5.45; N, 3.79. Found: C, 67.97; H, 5.47; N, 3.53.

Example 11

Preparation of 2-(4-Chlorobenzyl)-3-Hydroxy-6-Phenylquinoline-4-Carboxylic Acid (Compound 11)

This compound was prepared according to Scheme 12 below.

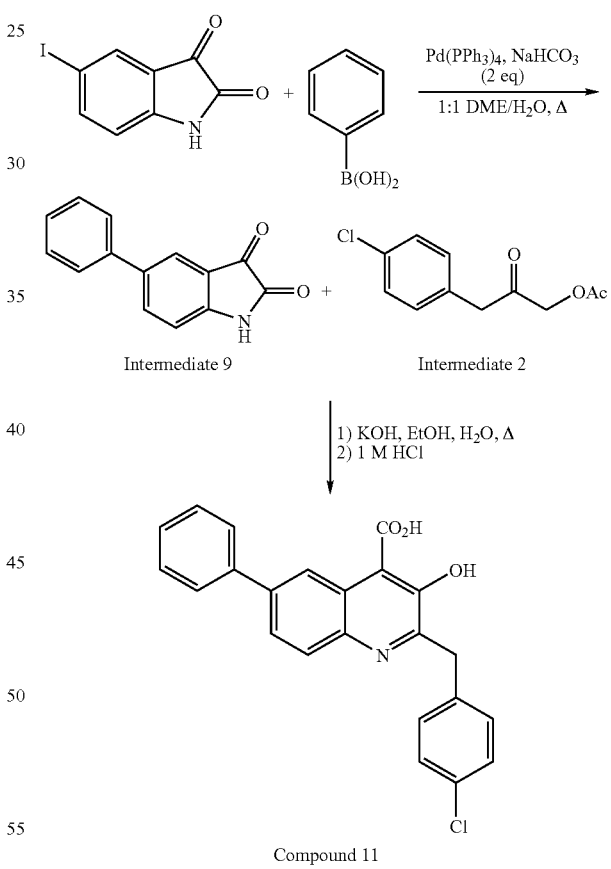

Scheme 12
Preparation of 2-(4-chlorobenzyl)-3-hydroxy-6-phenylquinoline-4-carboxylic acid (Compound 11)

Intermediate 9            Intermediate 2

Compound 11

Intermediate 9: 5-Phenyl-1H-indole-2,3-dione

The procedure described above for the synthesis of 7-(thien-3-yl)isatin, intermediate 8 was followed, reacting 5-iodoisatin (2.00 g, 7.33 mmol) with phenylboronic acid (0.983 g, 8.06 mmol) until LC-MS showed complete disappearance of 5-iodoisatin (2 hours). The crude isatin was purified by flash chromatography over silica gel (3% ethyl acetate in dichloromethane) to give pure intermediate 9 (0.73 g, 45% yield): ¹H NMR (400 MHz, DMSO-D₆) δ 7.01 (d, J=8.1 Hz, 1H) 7.36 (tt, 1H) 7.46 (t, J=7.5 Hz, 2H) 7.66 (m, 2H) 7.77 (d, J=2.0 Hz, 1H) 7.91 (dd, J=8.3, 2.0 Hz, 1H) 11.13 (s, 1H).

2-(4-chlorobenzyl)-3-hydroxy-6-phenylquinoline-4-carboxylic Acid (Compound 11)

The procedure described above for the synthesis of Compound 2 was followed, reacting 5-phenylisatin (0.73 g, 3.3 mmol) with 3-(4-chlorophenyl)-2-oxopropyl acetate (0.926 g, 4.09 mmol). The crude acid was then purified as described above for Compound 3 to give pure product as a bright yellow powder (Compound 11, 0.181 g, 14% yield): ¹H NMR (400 MHz, DMSO-D₆) δ 4.35 (s, 2H) 7.36 (s, 4H) 7.43 (t, J=7.3 Hz, 1H) 7.54 (t, J=7.6 Hz, 2H) 7.74 (d, J=7.3 Hz, 2H) 7.87 (dd, J=8.5, 1.9 Hz, 1H) 8.01 (d, J=8.6 Hz, 1H) 9.10 (br. s, 1H).

Example 12

Preparation of 2-(4-Chlorobenzyl)-8-(Fur-3-yl)-3-Hydroxyquinoline-4-Carboxylic Acid (Compound 12)

This compound was prepared according to Scheme 13 below.

Intermediate 10: 7-Furan-3-yl-1H-indole-2,3-dione

This compound was synthesized by the procedure described above for 7-(thien-3-yl)isatin, reacting 7-iodoisatin, intermediate 8 (2.00 g, 7.33 mmol) with 3-furanboronic acid (0.902 g, 8.06 mmol) until LC-MS showed complete disappearance of 7-iodoisatin (2 hours). The crude isatin was purified by flash chromatography over silica gel (3% ethyl acetate in dichloromethane) to give intermediate 10 of sufficient purity to be used in the next step: ¹H NMR (400 MHz, DMSO-D₆) δ 6.90 (dd, J=1.9, 0.9 Hz, 1H) 7.14 (t, 1H) 7.48 (dt, J=7.3, 1.0 Hz, 1H) 7.72 (dd, J=7.8, 1.3 Hz, 1H) 7.83 (t, 1H) 8.12 (t, 1H) 10.76 (s, 1H).

2-(4-chlorobenzyl)-8-(fur-3-yl)-3-hydroxyquinoline-4-carboxylic Acid (Compound 12)

This compound was synthesized according to the procedure described above for Compound 2, reacting 7-(fur-3-yl)isatin, Intermediate 10 (0.84 g, 3.9 mmol) with 3-(4-chlorophenyl)-2-oxopropyl acetate, Intermediate 2 (1.11 g, 4.91 mmol). The crude acid was purified as described above for Compound 3 to give pure product, a mustard-yellow powder Compound 12 (0.217 g, 15% yield): ¹H NMR (400 MHz, DMSO-D₆) δ 4.40 (s, 2H) 7.09 (d, J=1.8Hz, 1H) 7.39 (q, J=8.6 Hz, 4H) 7.56 (dd, J=8.46, 7.5 Hz, 1H) 7.67 (t, J=1.8 Hz, 1H) 7.84 (dd, J=7.3, 1.3 Hz, 1H) 8.07 (s, 1H) 8.30 (dd, J=8.6, 1.0 Hz, 1H).

Example 13

Preparation of 2-(4-Chlorobenzyl)-8-Fluoro-3-Hydroxyquinoline-4-Carboxylic Acid (Compound 13)

This compound was prepared according to Scheme 14 below.

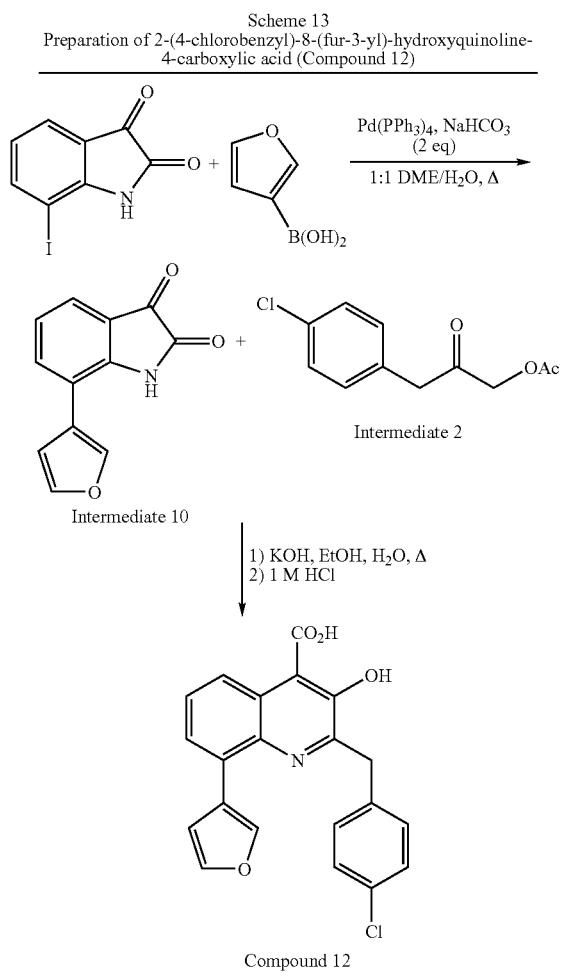

Scheme 13
Preparation of 2-(4-chlorobenzyl)-8-(fur-3-yl)-hydroxyquinoline-4-carboxylic acid (Compound 12)

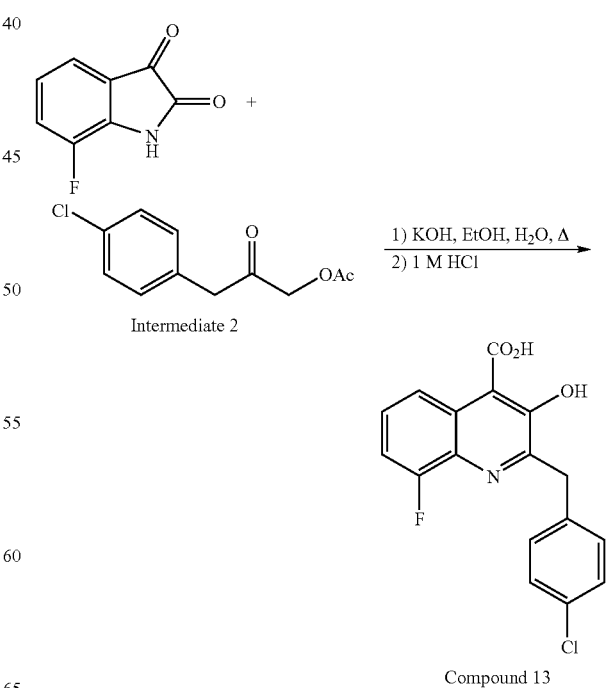

Scheme 14
Preparation of 2-(4-chlorobenzyl)-8-fluoro-3-hydroxyquinoline-4-carboxylic acid (Compound 13)

2-(4-chlorobenzyl)-8-fluoro-3-hydroxyquinoline-4-carboxylic Acid (Compound 13)

This compound was synthesized according to the procedure described above for Compound 2, reacting 7-fluoroisatin (1.00 g, 6.06 mmol) with 3-(4-chlorophenyl)-2-oxopropyl acetate, Intermediate 2 (1.72 g, 7.57 mmol). The crude acid was purified as described above for Compound 3, then recrystallized from ethanol/benzene to give pure product as an off-white powder Compound 13 (0.206 g, 10% yield): $^1$H NMR (400 MHz, DMSO-D$_6$) δ 4.34 (s, 2H) 7.37 (m, 5H) 7.55 (m, 1H) 8.34 (d, J=8.6 Hz, 1H).

Example 14

Preparation of 2-(4-Chloro-Benzyl)-3-Hydroxy-6-Trifluoromethoxy-Quinoline-4-Carboxylic Acid (Compound 14)

This compound was prepared according to Scheme 15 below.

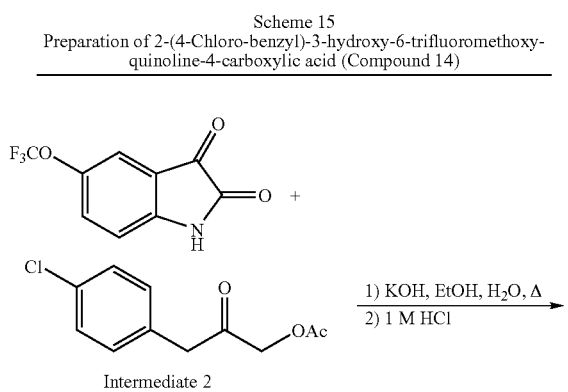

2-(4-Chloro-benzyl)-3-hydroxy-6-trifluoromethoxy-quinoline-4-carboxylic Acid (Compound 14)

This compound was synthesized according to the procedure described above for Compound 2, reacting 5-trifluoromethoxyisatin (1.4 g, 6.06 mmol) with 3-(4-chlorophenyl)-2-oxopropyl acetate, Intermediate 2 (1.72 g, 7.57 mmol). The crude acid was recrystallized from ethanol to give pure product as a yellow powder Compound 14 (1.2 g, 50% yield): $^1$H NMR (400 MHz, DMSO-D6) δ ppm 4.32 (s, 2H) 7.26-7.40 (m, 4H) 7.47 (d, J=9.09 Hz, 1H) 8.00 (d, J=8.84 Hz, 1H) 8.86 (s, 1H).

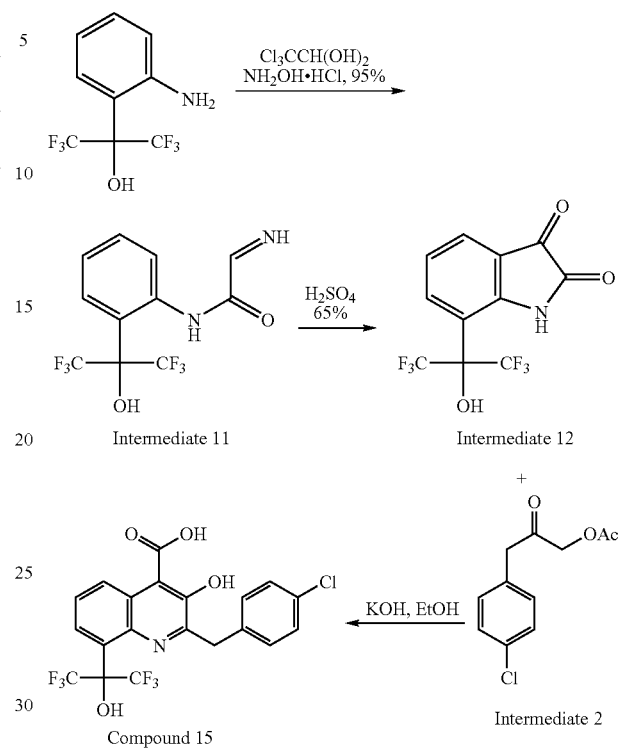

Example 15

Preparation of Compound 15

Intermediate 11: 2-Imino-N-[2-(2,2,2-trifluoro-1-hydroxy-1-trifluoromethyl-ethyl)-phenyl]-acetamide The isatin synthesis described by Yang et al. (*J. Am. Chem. Soc.*, 1996, 118, 9557) was used. A mixture of chloral hydrate (2.4 g, 14.9 mmol), hydroxylamine hydrochloride (3.3 g, 47.8 mmol), sodium sulfate (19 g, 133.8 mmol), 2-(2-amino-phenyl)-1,1,1,3,3,3-hexafluoro-propan-2-ol (12.6 mmol), aq. HCl (10 mL, 1N), and 90 mL water was stirred at 55° C. overnight. The reaction mixture was cooled to 25° C. The precipitate was collected by filtration, washed with water, and dried under vacuum overnight to provide the intermediate 11 which was used further without purification. 1H NMR (400 MHz, DMSO-D6) δ ppm 7.20-7.29 (m, 1H), 7.48-7.52 (m, 2H), 7.58 (s, 1H), 8.45 (m, 1H), 10.07 (s, 1H), 10.67 (s, 1H), 12.47 (s, 1H).

Intermediate 12: 7-(2,2,2-Trifluoro-1-hydroxy-1-trifluoromethyl-ethyl)-1H-indole-2,3-dione Intermediate 11 from above was mixed with 11 mL concentrated sulfuric acid at 25° C. The resulting solution was heated to 85° C. gradually and stayed at this temperature for 10 min. The reaction mixture was then cooled to 25° C. 50 mL crushed ice was added, and the reaction mixture was allowed to stay at 0° C. for 30 min. The precipitate was collected by filtration, washed with water, and dried under vacuum overnight to give isatin 12, which was used for the next step without further purification. $^1$H NMR (400 MHz, DMSO-D6)

δ ppm 7.14-7.33 (m, 1H), 7.47-7.55 (m, 1H), 7.60-7.72 (m, 1H), 9.45 (s, 1H), 12.48 (s, 1H).

2-(4-Chloro-benzyl)-3-hydroxy-8-(2,2,2-trifluoro-1-hydroxy-1-trifluoromethyl-ethyl)-quinoline-4-carboxylic Acid (Compound 15)

The procedure described by Cragoe et al. (*J. Org. Chem.*, 1953, 18, 561) was used. To a mixture of isatin 13 (3.48 mmol) in 2 mL EtOH and 4 mL aq. 6 M KOH at 100° C. was added warm 3-(4-chlorophenyl)-2-oxopropyl acetate (0.9 g, 3.98 mmol) in 2 mL EtOH in small portions over 1 hour period. After the addition was completed, the reaction mixture was refluxed for additional 1 h. Removal of the solvent, the resulting yellow gum was acidified with aq. 1 N HCl to pH~1. HPLC of the precipitate under basic conditions afforded solid, which was acidified at 0° C. with 1N aq. HCl to pH~1. The precipitate was collected by centrifuge, washed with water, and dried under vacuum to yield compound 15 as a beige solid. 1H NMR (400 MHz, DMSO-D6) δ ppm 4.28 (s, 2H), 7.26-7.42 (m, 4H), 7.53 (d, J=6.32 Hz, 1H), 7.53 (d, J=6.44 Hz, 1H), 9.60 (dd, J=6.32, 6.44 Hz, 1H), 13.22 (s, 1H).

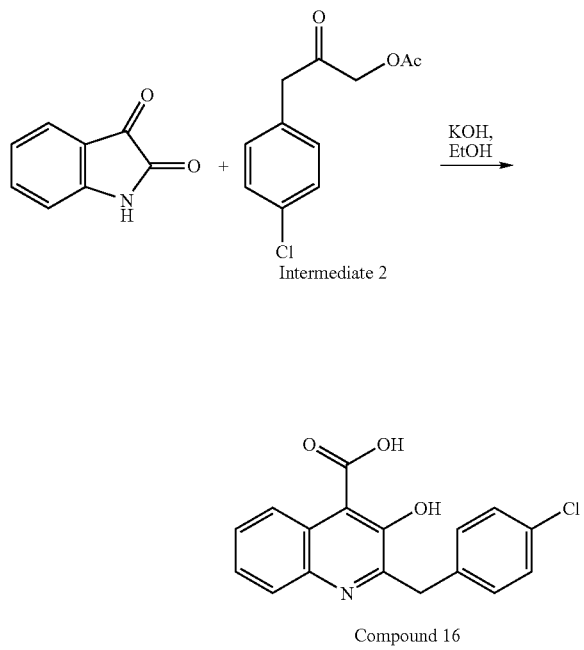

Synthesis of Compound 16

Example 16

Preparation of Compound 16

2-(4-chloro-benzyl)-3-hydroxy-quinoline-4-carboxylic Acid (compound 16)

The procedure described above for the synthesis of compound 15 was used to react isatin and 3-(4-chlorophenyl)-2-oxopropyl acetate to give compound 16 as an yellow solid. 1H NMR (400 MHz, DMSO-D6) δ ppm 4.36 (s, 2H), 7.26-7.42 (m, 5H), 7.51-7.68 (m, 2H), 7.88-8.02 (m, 1H), 8.78 (bs, 1H).

Example 17

Assay of Compounds of the Invention

Compounds of the invention can be assayed for selectin inhibitory activity using any of the procedures known in the art. One convenient procedure is the determination of IC50 values for inhibition of P-selectin binding to P-selectin glycoprotein ligand-1 (PSGL-1) using Biacore.

The Biacore 3000 is an instrument that uses surface plasmon resonance to detect binding of a solution phase analyte to an immobilized ligand on a sensor chip surface. The analyte sample is injected under flow using a microfluidic system. Binding of analyte to ligand causes a change in the angle of refracted light at the surface of the sensor chip, measured by the Biacore instrument in resonance units (RUs).

SGP-3 is a purified sulfoglycopeptide form of human PSGL-1 that contains the P-selectin binding determinants (See Somers et al., 2000, *Cell* 103, 467-479). SGP-3 was biotinylated via amine chemistry at a unique C-terminal lysine residue and immobilized on streptavidin-coated SA sensor chip. A solution containing a soluble recombinant truncated form of human P-selectin comprised of the lectin and EGF domains (P-LE) was delivered to the SGP-3 coated sensor chip. The P-LE solution contains 100 mM HEPES, 150 mM NaCl, 1 mM $CaCl_2$, 1 mM $MgCl_2$, 0.05% P40, 10% DMSO. $K_D$ values were typically calculated to be approximately 778+/−105 nM using this Biacore assay format (Somers et al., supra).

Small molecule P-selectin inhibitors are incubated for 1 hour in 100 mM HEPES, 150 mM NaCl, 1 mM $CaCl_2$, 1 mM $MgCl_2$, 0.05% P40, 10% DMSO, prior to introducing them into the Biacore 3000. Solutions are filtered if formation of precipitate is visible. Soluble P-LE is added to the small molecule solution at final concentrations 500 nM and 500 uM respectively. Sample injections are run in duplicates, and each compound is assayed at least twice.

The Biacore assay measures the signal in RU produced by binding of P-LE to SGP-3 in the presence and absence of inhibitors. Percent inhibition of binding is calculated by dividing the inhibited signal by the uninhibited signal subtracting this value from one then multiplying by one hundred. Inhibitors, with greater than 50% inhibition at 500 uM, are assayed again using a series of two fold dilutions. The data from this titration are plotted, RU values vs. concentration, and the IC50 is determined by extrapolation from the plot. All RU values are blank and reference subtracted prior to percent inhibition and IC50 determination. Glycerrhizzin is used as a positive control, inhibiting 50% at 1 mM.

Compounds 1-14 were assayed as described above. IC50 values for twelve of the compounds ranged from 125 μM to 1000 μM. One compound showed 23% inhibition at 1000 μM, and one compound showed no inhibition at 500 μM.

It is intended that each of the patents, applications, and printed publications including books mentioned in this patent document be hereby incorporated by reference in their entirety.

As those skilled in the art will appreciate, numerous changes and modifications may be made to the preferred embodiments of the invention without departing from the spirit of the invention. It is intended that all such variations fall within the scope of the invention.

What is claimed is:

1. A compound having the Formula II:

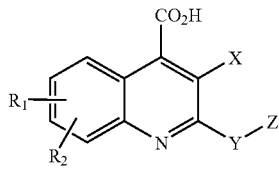

or a pharmaceutically acceptable salt thereof, wherein:

Y is O, $(CR_3R_4)_p$ or $NR_5$;

p is 1 to 3;

X is OH, $OR_3$, $OC_{1-6}$ alkyl, $OC(=O)$aryl, $OC(=O)C_{1-6}$ alkyl, $OC(=O)OC_{1-6}$ alkyl or $NR_3R_{3'}$;

each $R_1$, $R_2$ $R_3$, $R_{3'}$ and $R_4$ is independently hydrogen, $C_{1-6}$ alkyl, $C_{1-6}$ perhaloalkyl, $OC_{1-6}$ perhaloalkyl, halogen, thioalkyl, CN, OH, SH, $(CH_2)_nOSO_3H$, $(CH_2)_nSO_3H$, $(CH_2)_nCO_2R_6$, $OSO_3R_6$, $SO_2R_6$, $SO_3R_6$, $PO_3R_6R_7$, $(CH_2)_nSO_2NR_8R_9$, $(CH_2)_nC(=O)NR_8R_9$, $C(=O)R_{12}$, aryl, heterocyclo, $C(=O)$aryl, $C(=O)$heterocyclo, $OC(=O)$aryl, $OC(=O)$heterocyclo, Oaryl, Oheterocyclo, arylalkyl, $C(=O)$arylalkyl, $OC(=O)$arylalkyl, Oarylalkyl, alkenyl, alkynyl, or $NHCOR_8$, wherein any of said alkyl, Oalkyl, aryl, heterocyclo, $C(=O)$aryl, $C(=O)$heterocyclo, O—$C(=O)$aryl, O—$C(=O)$heterocyclo, O-aryl, O-heterocyclo, arylalkyl, $C(=O)$arylalkyl, O—$C(=O)$arylalkyl, O-arylalkyl, alkenyl or alkynyl can optionally be substituted with up to three substituents selected from halogen, $C_{1-6}$ alkyl, $OC_{1-6}$ alkyl and CN;

each $R_6$ and $R_7$ is independently selected from the group consisting of hydrogen and $C_{1-6}$ alkyl that is optionally substituted with up to three substituents selected from OH, $CF_3$, SH and halogen;

each $R_5$, $R_8$ and $R_9$ is independently selected from the group consisting of hydrogen, $C_{1-6}$ alkyl, $C_{1-6}$haloalkyl, thioalkyl, OH, $(CH_2)_1OSO_3H$, $(CH_2)_1SO_3R_{10}$, $(CH_2)_1CO_2R_{10}$, $SO_3R_{10}$, $PO_3R_{10}R_{11}$, $(CH_2)_1SO_2(CH_2)_n NR_{10}R_{11}$, $(CH_2)_1CONR_{10}R_{11}$, $COR_{10}$, aryl, heterocyclo, $C(=O)$aryl, $C(=O)$heterocyclo, O—$C(=O)$aryl, O—$C(=O)$heterocyclo, Oaryl, Oheterocyclo, arylalkyl, $C(=O)$arylalkyl, $OC(=O)$arylalkyl, Oarylalkyl, alkenyl, or alkynyl, wherein any of said alkyl, aryl, heterocyclo, $C(=O)$aryl, $C(=O)$heterocyclo, $OC(=O)$aryl, $OC(=O)$heterocyclo, Oaryl, Oheterocyclo, arylalkyl, $C(=O)$arylalkyl, $OC(=O)$arylalkyl, Oarylalkyl, alkenyl or alkynyl can optionally be substituted with up to three substituents selected from halogen, $C_{1-6}$ alkyl, $OC_{1-6}$ alkyl and CN;

each n is an independently selected integer from 0 to 6;

each l is an independently selected integer from 1 to 6;

each $R_{10}$ and $R_{11}$ is independently selected from the group consisting of hydrogen and $C_{1-6}$ alkyl that is optionally substituted with up to three substituents selected from OH, $CF_3$, SH and halogen;

each $R_{12}$ is independently hydrogen, $C_{1-6}$ alkyl, $C_{1-6}$ perhaloalkyl, $OC_{1-6}$ alkyl, $OC_{1-6}$ perhaloalkyl, thioalkyl, OH, $(CH_2)_1OSO_3H$, $(CH_2)_1SO_3H$, $(CH_2)_1CO_2R_6$, $(CH_2)_1SO_2NR_8R_9$, $(CH_2)_nC(=O)NR_8R_9$, $NR_8R_9$, alkenyl, alkynyl, or $NHCOR_8$, wherein any of said alkyl, Oalkyl, alkenyl or alkynyl can optionally be substituted with up to three substituents selected from halogen, $C_{1-6}$ alkyl, $OC_{1-6}$ alkyl and CN; and Z is aryl, arylalkyl, heteroaryl or heterocyclo, wherein each of said aryl, arylalkyl, heteroaryl and heterocyclo is optionally substituted.

2. The compound of claim 1 wherein Y is $CR_3R_4$.

3. The compound of claim 1 wherein Y is $CH_2$.

4. The compound of claim 1 wherein Y is $CH_2$ and X is OH.

5. The compound of claim 1 wherein Z is selected from:
   (a) a five-membered heterocyclic ring containing one to three ring heteroatoms selected from N, S or O; wherein said five-membered heterocyclic ring is optionally substituted by from 1 to 3 substituents selected from halogen, $C_{1-10}$ alkyl, $OC_{1-10}$ alkyl, $NO_2$, $NH_2$, CN, $CF_3$, and $CO_2H$;
   (b) a six-membered heterocyclic ring containing one to three ring heteroatoms selected from N, S or O; wherein said six-membered heterocyclic ring is optionally substituted by from 1 to 3 substituents selected from halogen, $C_{1-10}$ alkyl, $OC_{1-10}$ alkyl, CHO, $CO_2H$, $C(=O)R_{20}$, $SO_2R_{20}$, $NO_2$, $NH_2$, CN, $CF_3$ and OH; wherein each $R_{20}$ is independently selected from the group consisting of $C_{1-10}$ alkyl, $OC_{1-10}$ alkyl and $NR_6R_7$;
   (c) a bicyclic ring moiety optionally containing from 1 to 3 ring heteroatoms selected from N or O; wherein said bicyclic ring moiety is optionally substituted by from 1 to 3 substituents selected from halogen, $C_{1-6}$ alkyl, $OC_{1-6}$ alkyl, CHO, $NO_2$, $NH_2$, CN, $CF_3$, $CO_2H$, $C(=O)R_{20}$, $SO_2R_{20}$, and OH; and
   (d) a benzyl, naphthyl, or phenyl ring, each of which is optionally substituted by from 1 to 3 substituents selected from halogen, $C_{1-6}$ alkyl, phenyl, benzyl, Ophenyl, Obenzyl, $SO_2NH_2$, $SO_2NH(C_{1-6}$ alkyl), $SO_2N(C_{1-16}$ alkyl$)_2$, $CH_2COOH$, $CO_2H$, $CO_2Me$, $CO_2Et$, $CO_2iPr$, $C(=O)NH_2$, $C(=O)NH(C_{1-16}$ alkyl), $C(=O)N(C_{1-6}$ alkyl$)_2$, OH, $SC_{1-6}$ alkyl, $OC_{1-6}$ alkyl, $NO_2$, $NH_2$, $CF_3$, and CN.

6. The compound of claim 1 wherein Z is aryl.

7. The compound of claim 1 wherein $R_1$ and $R_2$ are each independently hydrogen, $C_{1-6}$ alkyl, $C_{1-6}$ perhaloalkyl, $OC_{1-6}$ alkyl, $OC_{1-6}$ perhaloalkyl, halogen, thioalkyl, CN, OH, SH, $(CH_2)_nOSO_3H$, $(CH_2)_nSO_3H$, $(CH_2)_nCO_2R_6$, $OSO_3R_6$, $SO_3R_6$, $PO_3R_6R_7$, $(CH_2)_nSO_2NR_8R_9$, $(CH_2)_nC(=O)NR_8R_9$, $NR_8R_9$, aryl, heterocyclo, $C(=O)R_{12}$, $C(=O)$aryl, $C(=O)$heterocyclo, $OC(=O)$aryl, $OC(=O)$heterocyclo, Oaryl, Oheterocyclo, $C(=O)$arylalkyl, $OC(=O)$arylalkyl, Oarylalkyl, alkenyl, alkynyl, or $NHCOR_8$.

8. The compound of claim 1 wherein
Y is $CH_2$, X is OH, and Z is selected from:
   (a) a five-membered heterocyclic ring containing one to three ring heteroatoms selected from N, S or O; wherein said five-membered heterocyclic ring is optionally substituted by from 1 to 3 substituents selected from halogen, $C_{1-10}$ alkyl, $OC_{1-10}$ alkyl, $NO_2$, $NH_2$, CN, $CF_3$, and $CO_2H$;
   (b) a six-membered heterocyclic ring containing one to three ring heteroatoms selected from N, S or O; wherein said six-membered heterocyclic ring is optionally substituted by from 1 to 3 substituents selected from halogen, $C_{1-10}$ alkyl, $OC_{1-10}$ alkyl, CHO, $CO_2H$, $C(=O)R_{20}$, $SO_2R_{20}$, $NO_2$, $NH_2$, CN, $CF_3$ and OH;
   (c) a bicyclic ring moiety optionally containing from 1 to 3 ring heteroatoms selected from N or O; wherein said bicyclic ring moiety is optionally substituted by from 1 to 3 substituents selected from halogen, $C_{1-6}$ alkyl, $OC_{1-6}$ alkyl, CHO, $NO_2$, $NH_2$, CN, $CF_3$, $CO_2H$, $C(=O)R_{20}$, $SO_2R_{20}$, and OH; and
   (d) a benzyl, naphthyl, or phenyl ring, each of which is optionally substituted by from 1 to 3 substituents selected from halogen, $C_{1-6}$ alkyl, phenyl, benzyl, Ophenyl, Obenzyl, $SO_2NH_2$, $SO_2NH(C_1alkyl)$, $SO_2N(C_1-1$ alkyl$)_2$, $CH_2COOH$, $CO_2H$, $CO_2Me$, $CO_2Et$, $CO_2iPr$, $C(=O)NH_2$, $C(=O)NH(C_{1-6}$ alkyl), $C(=O)N(C_{1-6}$ alkyl$)_2$, OH, $SC_{1-6}$ alkyl, $OC_{1-6}$ alkyl, $NO_2$, $NH_2$, $CF_3$, and CN.

9. The compound of claim 1 having the Formula III:

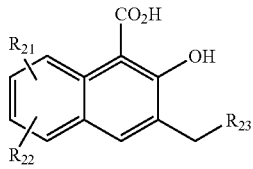

or a pharmaceutically acceptable salt thereof,
wherein:
$R_{21}$, and $R_{22}$ are independently, H, halogen, OH, CN, SH, $C_{1-6}$ alkyl, $OC_{1-6}$ alkyl, $C_{1-6}$ perhaloalkyl, $C_{1-6}$ thioalkyl, aryl or heteroaryl;
wherein said aryl and said heteroaryl can each optionally be substituted with up to three substituents selected from halogen, OH, CN, SH, $NH_2$, $C_{1-6}$ alkyl, $OC_{1-6}$ alkyl, $C_{1-6}$ perhaloalkyl and $C_{1-6}$ thioalkyl; and
wherein said $C_{1-6}$ alkyl, $OC_{1-6}$ alkyl and $C_{1-6}$ thioalkyl can each optionally be substituted with up to three substituents selected from halogen, OH, CN, SH, $NH_2$, $OC_{1-6}$ alkyl, $C_1$ perhaloalkyl and $C_{1-6}$ thioalkyl; and
$R_{23}$ is aryl or heteroaryl, wherein said aryl and said heteroaryl can each optionally be substituted with up to three substituents selected from halogen, OH, CN, SH, $NH_2$, $C_{1-6}$ alkyl, $OC_{1-6}$ alkyl, $C_{1-6}$ perhaloalkyl and $C_{1-6}$ thioalkyl.

10. The compound of claim 9 wherein:
$R_{21}$, and $R_{22}$ are independently selected from the group consisting of H, $C_{1-6}$ alkyl, halogen, aryl, heteroaryl, and $OC_{1-6}$ alkyl wherein said heteroaryl is 3-furanyl or 3-thiophenyl and said aryl is unsubstituted phenyl; and said $C_{1-6}$ alkyl and said $OC_{1-6}$ alkyl can each optionally be substituted with up to three substituents selected from halogen, OH, CN, SH, $NH_2$, $OC_{1-6}$ alkyl, $C_{1-6}$ perhaloalkyl and $C_{1-6}$ thioalkyl; and
$R_{23}$ is a phenyl group substituted at the 4'-position with halogen, $C_{1-6}$ alkyl, $SC_{1-6}$ alkyl, or $OC_{1-6}$ alkyl.

11. The compound of claim 1 wherein $R_1$ and $R_2$ are located on the 7 and 8 positions of the quinoline ring and are independently selected from the group consisting of H, methyl, and unsubstituted phenyl; and
$R_{23}$ is phenyl substituted at the 4'-position with Cl or $OCF_3$.

12. The compound of claim 1 wherein:
$R_1$ is located at the 7 position of the quinoline ring and $R_2$ is located at the 8 position of the quinoline ring; and either:
$R_1$ is $CH_3$, $R_2$ is $CH_3$ and $R_{23}$ is 4-chlorophenyl; or
$R_1$ is H, $R_2$ is unsubstituted phenyl and $R_{23}$ is 4-chlorophenyl.

13. The compound of claim 1 that is 2-(4-chloro-benzyl)-3-hydroxy-7,8,-dimethyl-quinoline-4-carboxylic acid.

14. The compound of claim 1 that is 2-(4-chloro-benzyl)-3-hydroxy-8-phenyl-quinoline-4-carboxylic acid.

15. The compound of claim 1 that is selected from the group consisting of:
a) 2-(4-Chloro-benzyl)-3-hydroxy-8-trifluoromethyl-quinoline-4-carboxylic acid;
b) 2-(4-Chloro-benzyl)-3-hydroxy-8-trifluoromethoxy-quinoline-4-carboxylic acid;
c) 2-(4-Chlorobenzyl)-3-hydroxy-8-isopropylquinoline-4-carboxylic acid;
d) 2-(4-Chlorobenzyl)-3-hydroxy-8-methylquinoline-4-carboxylic acid;
e) 2-(4-Chlorobenzyl)-8-ethyl-3-hydroxyquinoline-4-carboxylic acid;
f) 2-(4-Chlorobenzyl)-3-hydroxy-8-(thien-3-yl)quinoline-4-carboxylic acid;
g) 8-Bromo-2-(4-chlorobenzyl)-3-hydroxyquinoline-4-carboxylic acid;
h) 8-(sec-Butyl)-2-(4-chlorobenzyl)-3-hydroxyquinoline-4-carboxylic acid;
i) 2-(4-Chlorobenzyl)3-hydroxy-6-phenylquinoline-4-carboxylic acid;
j) 2-(4-Chlorobenzyl)-8-(fur-3-yl)-3-hydroxyquinoline-4-carboxylic acid;
k) 2-(4-Chlorobenzyl)-8-fluro-3-hydroxyquinoline-4-carboxylic acid; and
l) 2-(4-Chlorobenzyl)-8-fluoro-3-hydroxyquinoline-4-carboxylic acid;
m) 2-(4-Chloro-benzyl)-3-hydroxy-8-(2,2,2-trifluoro-1-hydroxy-1-trifluoro methyl-ethyl)-quinoline-4-carboxylic acid; and
n) 2-(4-Chloro-benzyl)-3-hydroxy-quinoline-4-carboxylic acid.

16. A composition comprising a compound of claim 1 and one or more pharmaceutically acceptable carriers.

* * * * *

UNITED STATES PATENT AND TRADEMARK OFFICE
CERTIFICATE OF CORRECTION

PATENT NO.         : 7,465,799 B2
APPLICATION NO.    : 10/984093
DATED              : December 16, 2008
INVENTOR(S)        : Kaila et al.

It is certified that error appears in the above-identified patent and that said Letters Patent is hereby corrected as shown below:

On the Title Page

Item (75); Page 1, in the first column, the inventor "Kristin M. Jantz" should be
-- Kristin M. Janz --.

In the Claims

In column 39, line 18, Claim No. 1:
    Change "$R_2 R_3$" to -- $R_2$, $R_3$ --.

In column 39, lines 48-49, Claim No. 1:
    Replace "aryla-lkyl" with -- arylalkyl --.

In column 40, line 32, Claim No. 5:
    Change "$SO_2N(C_1.16\ alkyl)_2$" to -- $SO_2N(C_{1-16}\ alkyl)_2$ --.

In column 40, line 33, Claim No. 5:
    Change "$C(=O)NH(C_1-16\ alkyl)$" to -- $C(=O)NH(C_{1-16}\ alkyl)$ --.

In column 41, line 6, Claim No. 8:
    After "and CN" insert -- wherein each $R_{20}$ is independently selected from the group consisting of $C_{1-10}$alkyl, $OC_{1-10}$alkyl and $NR_6R_7$ --.

In column 41, line 47, Claim No. 11:
    Change "claim 1" to read -- claim 9 --.

UNITED STATES PATENT AND TRADEMARK OFFICE
CERTIFICATE OF CORRECTION

PATENT NO. : 7,465,799 B2
APPLICATION NO. : 10/984093
DATED : December 16, 2008
INVENTOR(S) : Kaila et al.

It is certified that error appears in the above-identified patent and that said Letters Patent is hereby corrected as shown below:

In column 42, line 4, Claim No. 11:
 Change "claim 1" to read -- claim 9 --.

Signed and Sealed this

Twenty-first Day of April, 2009

JOHN DOLL
*Acting Director of the United States Patent and Trademark Office*